United States Patent
Weiler et al.

(10) Patent No.: US 11,278,074 B2
(45) Date of Patent: *Mar. 22, 2022

(54) METHODS OF MONITORING A BODY PART OF A PERSON AND FITTING COMPRESSION GARMENTS THERETO

(71) Applicants: Michael J. Weiler, Atlanta, GA (US); Nathan Daniel Frank, Atlanta, GA (US)

(72) Inventors: Michael J. Weiler, Atlanta, GA (US); Nathan Daniel Frank, Atlanta, GA (US)

(73) Assignee: LYMPHATECH, Atlanta, GA (US)

( * ) Notice: Subject to any disclaimer, the term of this patent is extended or adjusted under 35 U.S.C. 154(b) by 266 days.

This patent is subject to a terminal disclaimer.

(21) Appl. No.: 16/357,090

(22) Filed: Mar. 18, 2019

(65) Prior Publication Data

US 2019/0208850 A1 Jul. 11, 2019

Related U.S. Application Data

(63) Continuation of application No. 15/896,765, filed on Feb. 14, 2018, which is a continuation-in-part of application No. 15/674,152, filed on Aug. 10, 2017.
(Continued)

(51) Int. Cl.
*A41H 3/00* (2006.01)
*G05B 19/4097* (2006.01)
(Continued)

(52) U.S. Cl.
CPC ............... *A41H 3/007* (2013.01); *A41H 3/04* (2013.01); *A61H 1/008* (2013.01);
(Continued)

(58) Field of Classification Search
CPC ............ A41H 3/007; G06T 7/55; G06T 7/60; G06T 2707/30196; G06T 2207/30196; A61H 1/008; G05B 19/4097; G05B 2219/2653
(Continued)

(56) References Cited

U.S. PATENT DOCUMENTS 4,406,544 A 9/1983 Takada et al.
4,885,844 A 12/1989 Chun
(Continued)

FOREIGN PATENT DOCUMENTS

CN 104809639 A 7/2015
EP 1616281 B1 1/2006
(Continued)

OTHER PUBLICATIONS

International Search Report and Written Opinion for related PCT Application No. PCT/US2017-046325, filed Aug. 10, 2017, dated Oct. 18, 2017.
(Continued)

*Primary Examiner* — Nathan E Durham
(74) *Attorney, Agent, or Firm* — Thomas | Horstemeyer, LLP

(57) ABSTRACT

The present invention relates to methods of fitting for pre-fabricated compression garments via digital imaging of a wearer body part and measurement of body part circumferences and, optionally, lengths therefrom. The present invention also relates to methods of generating a shape description derived from digital imaging of a patient body part or body area of interest and use of such shape description. Such shape description includes geometric information from which measurement information can optionally be derived. Included herein are methods for diagnosing and monitoring edema and other conditions in patients using
(Continued)

shape descriptions acquired from a patient in need of such diagnosis and monitoring. The invention also includes use of the generated shape descriptions to make compression garments specifically configured for a patient's body part or body area. Compression garments generated from the generated shape descriptions are also included herein.

17 Claims, 10 Drawing Sheets

Related U.S. Application Data

(60) Provisional application No. 62/372,891, filed on Aug. 10, 2016.

(51) Int. Cl.
| | | |
|---|---|---|
| *G16H 30/20* | (2018.01) | |
| *G06T 7/60* | (2017.01) | |
| *G16H 30/40* | (2018.01) | |
| *A41H 3/04* | (2006.01) | |
| *G16H 50/50* | (2018.01) | |
| *A61H 1/00* | (2006.01) | |

(52) U.S. Cl.
CPC ............ *G05B 19/4097* (2013.01); *G06T 7/60* (2013.01); *G16H 30/20* (2018.01); *G16H 30/40* (2018.01); *G16H 50/50* (2018.01); *A61H 2205/00* (2013.01); *G05B 2219/2652* (2013.01); *G06T 2200/04* (2013.01); *G06T 2200/08* (2013.01); *G06T 2207/30004* (2013.01); *G06T 2207/30196* (2013.01)

(58) Field of Classification Search
USPC .................................................. 700/130–132
See application file for complete search history.

(56) References Cited

U.S. PATENT DOCUMENTS

| | | | |
|---|---|---|---|
| 5,450,750 | A | 9/1995 | Abler |
| 5,530,652 | A | 6/1996 | Croyle et al. |
| 6,415,199 | B1 | 7/2002 | Liebermann |
| 6,463,351 | B1 | 10/2002 | Clynch |
| 6,546,309 | B1 | 4/2003 | Gazzuolo |
| 6,888,640 | B2 | 5/2005 | Spina et al. |
| 6,927,858 | B2 | 8/2005 | Boone et al. |
| 7,039,486 | B2 | 5/2006 | Wang |
| 7,043,329 | B2 | 5/2006 | Dias et al. |
| 7,092,782 | B2 | 8/2006 | Lee |
| 7,398,133 | B2 | 7/2008 | Wannier et al. |
| 7,421,306 | B2 | 9/2008 | Adiseshan |
| 7,594,896 | B2 | 9/2009 | Sakai et al. |
| 7,615,018 | B2 | 11/2009 | Nelson et al. |
| 8,387,266 | B2 | 3/2013 | Eddy |
| 8,491,514 | B2 | 7/2013 | Creighton et al. |
| 8,813,378 | B2 | 8/2014 | Grove |
| 9,345,271 | B2 | 5/2016 | Collins et al. |
| 10,251,438 | B2 | 4/2019 | Weiler |
| 2002/0004763 | A1 | 1/2002 | Lam |
| 2002/0138170 | A1 | 9/2002 | Onyshkevych et al. |
| 2002/0178061 | A1 | 11/2002 | Lam |
| 2002/0188372 | A1 | 12/2002 | Lane et al. |
| 2005/0049741 | A1* | 3/2005 | Dias ................. D04B 37/02 700/141 |
| 2005/0154487 | A1 | 7/2005 | Wang |
| 2006/0287877 | A1 | 12/2006 | Wannier et al. |
| 2007/0005174 | A1 | 1/2007 | Thomas |
| 2008/0255920 | A1 | 10/2008 | Vandergriff et al. |
| 2009/0099457 | A1 | 4/2009 | Barnes |
| 2009/0234489 | A1 | 9/2009 | Healy |
| 2009/0316965 | A1 | 12/2009 | Mailling et al. |
| 2010/0023421 | A1 | 1/2010 | Wannier et al. |
| 2010/0056973 | A1 | 3/2010 | Farrow et al. |
| 2010/0312143 | A1 | 12/2010 | Kim |
| 2011/0298897 | A1 | 12/2011 | Sareen et al. |
| 2012/0041344 | A1 | 2/2012 | Flodmark |
| 2014/0052028 | A1 | 2/2014 | Wright et al. |
| 2014/0200494 | A1 | 7/2014 | Winkler, Sr. et al. |
| 2014/0259267 | A1 | 9/2014 | Nordstrom |
| 2014/0277663 | A1 | 9/2014 | Gupta et al. |
| 2014/0300907 | A1 | 10/2014 | Kimmel |
| 2015/0051524 | A1 | 2/2015 | Messier |
| 2015/0081472 | A1 | 3/2015 | Levin et al. |
| 2015/0216477 | A1 | 8/2015 | Sayegh |
| 2015/0302594 | A1 | 10/2015 | Moore et al. |
| 2016/0120734 | A1 | 5/2016 | Ishikawa et al. |
| 2016/0235354 | A1 | 8/2016 | Weiler et al. |
| 2018/0042322 | A1 | 2/2018 | Weiler et al. |

FOREIGN PATENT DOCUMENTS

| | | | |
|---|---|---|---|
| EP | 1756343 | A1 | 2/2007 |
| EP | 1882447 | | 1/2008 |
| EP | 1444393 | B1 | 7/2010 |
| EP | 3525208 | B1 | 8/2019 |
| WO | 2005106087 | A1 | 11/2005 |
| WO | 2007085864 | A2 | 8/2007 |
| WO | 2014037939 | A1 | 3/2014 |
| WO | 2015120271 | A1 | 1/2015 |
| WO | 2015103620 | A1 | 7/2015 |
| WO | 2015120271 | | 8/2015 |
| WO | 2015155331 | | 10/2015 |

OTHER PUBLICATIONS

Nelson, Tyler S., et al. "Minimally invasive method for determining the effective lymphatic pumping pressure in rats using near-infrared imaging." American Journal of Physiology-Regulatory, Integrative and Comparative Physiology 306.5 (Jan. 2014): R281-R290.
Weiler, Michael, Timothy Kassis, and J_ Brandon Dixon. "Sensitivity analysis of near-infrared functional lymphatic imaging." Journal of biomedical optics 17.6 (Jun. 2012): 0660191-06601911.
The Diagnosis and Treatment of Lymphadema, The NLN Medical Advisory Committee, Updated Feb. 2011 available at http://www.lymphnel.org/pdfDocs/nIntreatmenl.pdf).
Weiler, Michael, and J_ Brandon Dixon. "Differential transport function of lymphatic vessels in the rat tail model and the long-term effects of Indocyanine Green as assessed with near-infrared imaging." Frontiers in physiology 4 (Aug. 2013).
Dixon, J. Brandon, and Michael J. Weiler. "Bridging the divide between pathogenesis and detection in lymphedema" Seminars in cell & developmental biology vol. 38. Academic Press (Feb. 2015).
Belbasis, Aaron, Franz Konstantin Fuss, and Jesper Sidhu. "Muscle activity analysis with a smart compression Jarmenl." Procedia Engineering 112 (Jan. 2015): 163-168.
Belbasis, Aaron, and Franz Konstantin Fuss. "Development of next-generation compression apparel." Procedia Technology 20 (Jan. 2015): 85-90.
Venkatraman, Praburaj, and D. J_ Tyler. "Applications of Compression Sportswear." Materials and Technology for Sportswear and Performance Apparel (Dec. 2015): 171-203.
Perrey, Stephana. "Compression garments: Evidence for their physiological effects (P208)." The Engineering of Sport 7 (2008): 319-28.
Kuking, Peter, et al. "Comparison of non-invasive individual monitoring of the training and health of athletes with Commercially available wearable technologies." Frontiers in physiology 7 (Mar. 2016).
European Application No. 17/840,289 Search Report dated Jan. 29, 2019.
Salleh M.N. et al: "Development of a flexible customized compression garment design system", Advanced Mechatronic Systems (ICAMECHS), 2012 International Conference on, IEEE, (2012) pp. 175-179.
R.C. Gonzalez and R.E. Woods, Digital Image Processing, Englewood Cliffs, NJ: Prentice Hall, 2007, Chapter 11 presentation by authors.

(56) References Cited

OTHER PUBLICATIONS

Volotao, Carlos FS, et al. "Shape characterization with turning functions," Proceedings of the 17th International Conference on Systems, Signals and Image Processing, Editora da Universidade Federal Fluminense vol. 1, 2010.
U.S. Appl. No. 15/674,152, Non-Final Office Action dated Dec. 19, 2017.
U.S. Appl. No. 15/674,152, Response to Non-Final Office Action dated Dec. 19, 2017.
U.S. Appl. No. 15/674,152, Notice of Allowance dated Jul. 11, 2018.
U.S. Appl. No. 15/896,765, Non-Final Office Action dated Apr. 19, 2018.
U.S. Appl. No. 15/896,765, Response to Non-Final Office Action dated Apr. 19, 2018.
U.S. Appl. No. 15/896,765, Notice of Allowance dated Nov. 9, 2018.
EP Search report for EP19155337.9 dated Jun. 7, 2019.
D'appuzo, et al., "Human body measurement newsletter you press teh button—we do the rest", Aug. 1, 2020, (Aug. 1, 2009), vol. 4, No. 1.
Homepage of Bauerfeind AG from 2016.
Bauerfeind Magizin, Life (2013).
BodyTronic 600—Bauerfeind (May 2017).
Screenshot of the the hompage of Bauerfeind AG showing the "Wayback Machine".
Muller, et al., A data-driven approach for real-time full body pose reconstruction from a depth camera, ResearchGate, Nov. 21.

\* cited by examiner

METHODS OF MONITORING A BODY PART OF A PERSON AND FITTING COMPRESSION GARMENTS THERETO

CROSS REFERENCE TO RELATED APPLICATIONS

This application is a Continuation of and claims priority to U.S. patent application Ser. No. 15/896,765, filed Feb. 14, 2018, which is a Continuation in Part from and claims priority to U.S. patent application Ser. No. 15/674,152, filed Aug. 10, 2017, which claims priority to and the benefit of U.S. Provisional Application No. 62/372,891, filed on Aug. 10, 2016. The disclosure of all of these applications are incorporated herein in their entirety by this reference.

FIELD OF THE INVENTION

The present invention relates to methods of fitting for pre-fabricated compression garments via digital imaging of a wearer body part and measurement of body part circumferences and, optionally, lengths therefrom. The present invention also relates to methods of generating a shape description derived from digital imaging of a patient body part or body area of interest and use of such shape description. Such shape description includes geometric information from which measurement information can optionally be derived. Included herein are methods for diagnosing and monitoring edema and other conditions in patients using shape descriptions acquired from a patient in need of such diagnosis and monitoring. The invention also includes use of the generated shape descriptions to make compression garments specifically configured for a patient's body part or body area. Compression garments generated from the generated shape descriptions are also included herein.

BACKGROUND OF THE INVENTION

"Edema" is the accumulation of excess fluid in a fluid compartment. This accumulation can occur in the cells (i.e., cellular edema), in the intercellular spaces within tissue (i.e., interstitial edema), or in other spaces in the body. Edema can be caused by a variety of factors, including indications associated with osmotic pressure, such as hypotonic fluid overload, which allows the movement of water into the intracellular space, or hypoproteinemia, which decreases the concentration of plasma proteins and permits the passage of fluid out of the blood vessels in to the tissue spaces. Other factors can include poor lymphatic drainage (known as "lymphedema"), conditions associated with an increased capillary pressure (e.g., excessive retention of salt and/or water), heart failure, and conditions associated with increased capillary pressure, such as inflammation.

When a person is symptomatic of edema, early diagnosis and treatment is imperative. As swelling increases, more pressure is exerted on surrounding cells, tissues and blood vessels. As these areas are squeezed from the increase of fluid and from the natural body response to increased inflammation (as a component of "first response" to an injury), more tissues die, more fluids are released, and the amount of edema presented increases. As edema increases, there is more potential for this "cascade effect" to continue, to result in even more damage. Thus, early diagnosis and regular patient monitoring can be critical to identify swelling occurring prior to the generation of the "edema cascade."

Compression garments can be used to prevent and or treat edema and a number of conditions that cause swelling in patient body parts or body areas. In this regard, edema, which as indicated, presents as excessive interstitial fluid accumulation, may arise from a variety of illnesses and conditions, including venous valvular insufficiency, post-phlebitic syndrome, posttraumatic swelling, postoperative swelling, congestive heart failure-related swelling, hypoalbuminemia-related swelling, drug induced swelling, and lymphedema.

In the treatment of edema-like conditions, compression garments can address patient body part or body area swelling by increasing transport and reducing stagnation of interstitial fluids. Such interstitial fluids operate to increase nutrient delivery to tissue, remove waste from tissues, reduce pain from swelling, and decrease the risk of infection.

For therapeutic use, that is, compression that is prescribed by a clinician for treatment of one or more medical indications, proper fitting of compression garments is important if only because ill-fitting garments will not provide the intended/prescribed amount of compression therapy to the person being treated. Existing methods of fitting compression garments for a specific patient are problematic, however. As would be understood, human body parts or body areas that may be fitted with compression garments are not regularly shaped, and some may be quite complex in surface shape or morphology, such as in patients with advanced lymphedema or those who are morbidly obese, for example.

A further concern in the design of a therapeutic compression garment is patient comfort. A compression garment may provide proper compression characteristics, but if the wearer experiences discomfort due to pinching, chaffing, buckling, or other reasons, she is unlikely to be compliant in wearing the compression garment and, thus, may not achieve therapeutic benefits. For example, the noncompliance rate for graduated compression stockings has been reported to be 30%-65%. Commonly cited reasons include, among other things, pain, discomfort, difficulty donning the stockings, perceived ineffectiveness, excessive heat, and skin irritation. Of course, if a patient fails to wear a compression garment that is prescribed for a potentially chronic or already chronic condition, that condition can become worse and, perhaps, irreversible damage could result. Thus, improved patient compression garment compliance is a need today.

Given the vast variation in human body shapes, custom garments can be indicated to provide optimum therapeutic benefits. Traditionally, compression garment fitting has been conducted primarily by use of a tape measure. While tape measurement techniques are widely available to a broad scope of medical providers, the technique generally suffers from poor accuracy. In short, tape measurement is not a very effective garment measurement tool because the technique has been shown to exhibit as much as an about 8 to about 12% inaccuracy due to inter and intra-operator variability. Such variability gives rise to a need for methods of measurement that demonstrate improvements in both accuracy and precision.

In therapeutic settings, patients often receive a recommendation for a custom fit garment, even though a custom fit garment is often far more expensive than an pre-fabricated compression garment. The time needed to generate such custom fit garments is long: the patient must be measured by a trained technician, and such measurements must be forwarded to a garment manufacturer, before the garments can be placed in a queue for manufacturing.

As noted, the current methodology used to fit compression garments is often inaccurate. Thus, using current fitting methodology, even expensive custom fit garments may not fit properly even when they are new. This means that, once the garments are sent back from the manufacturer, the fit quality must be checked by the technician and/or medical provider to make sure that the fit is therapeutically correct, thus necessitating further delays and increased cost in ensuring proper patient treatment. Often these custom-made compression garments must be remade; the fit error rate has been estimated to be from about 15 to about 40%. For chronic conditions, such as lymphedema or diabetic limb indications, such delay can cause irreversible harm to the patient. As a general rule, compression garments are usually only guaranteed to be therapeutically effective for a life of six months, this cycle must be repeated regularly, which can reduce patient compliance, as well as greatly adding to the cost of treatment given the high amount of in-person time a patient requires to ensure proper fit of the compression garment.

In addition to therapeutic effectiveness, compression garments are an increasingly popular clothing item worn by athletes and active individuals with the goal of enhancing recovery from exercise. As a general rule in medicine, particularly in orthopedics, when people have pain or instability, compression provides some improvement in symptoms. While the actual mechanism of action for compression clothing in athletic-type uses remains largely unknown today, it is generally hypothesized that when compression garments are used during recovery after exercise, muscle swelling is reduced. Improvements in recovery after exercise are seen by both men and women, who can be well-trained athletes or "weekend warriors." Generally, it seems likely that compression garments display greater overall benefits following higher amounts of, or greater intensities of, exercise. Some research indicates that compression garments may provide a "placebo effect" for users. Nonetheless, such a "placebo effect" may be beneficial if only because it increases the likelihood that a person will continue to exercise because they do not feel as injured.

Notwithstanding the lack of clear knowledge about how compression garments assist in athletic recovery, it is important to provide persons in need of treatment with compression garments that fit well. The question of fit, or more specifically, the degree of compression provided by compression garments to athletes, is a common issue that has been raised in the peer review process and literature regarding the variable results. Specifically, a large majority of studies have not measured the exact amount of compression that study participants are receiving. If compression is not optimized, then the garment cannot provide effective action to an athlete, regardless of whether that compression can actually make any physiological difference to an athlete.

In other words, the absence of consistent scientific data showing that compression garments are genuinely effective for assisting athletes is confused by the fact that compression garments that apply adequate compression for an athlete in need of compression have not been part of existing study protocols. Indeed, the fit of a compression garment for use by an athlete is critical: if compression in that athlete is not optimized, then the garment cannot do what it is proposed to do regardless of whether that compression can actually make any physiological difference to an athlete. While it is possible that an optimal degree of pressure(s) that elicits beneficial or better effects for athletic performance, there does not exist in the prior art a valid and reliable scientific method to measure the pressure at the garment-skin interface. While several studies reported attempts to quantify the degree of compression, these studies generally failed to report the reliability of these measurements. Moreover, attempts to measure compression have occurred at a small number of easily accessible sites that are not representative of the net compression over the entire limb.

As with compression garments intended for use to treat edema-like conditions, athletes can acquire custom fitted garments. The cost of such "bespoke" compression garments generally likely exceeds the perceived value of the garment for most people, however, especially when coupled with the current lack of scientifically reliable data on the use of compression garments in treating recovery after athletic activity. Moreover, as in the clinical treatment of edema-like conditions, existing methods of generating custom compression garments cannot accurately measure the shape of a body part in need of compression along the entire surface thereof. This leads again back to the issue of not knowing whether compression garments are actually beneficial to athletes because it has been too difficult to generate compression garments that can, in fact, apply therapeutic amounts of compression to an athlete. In short, the fit of the compression garment is an important factor in how effective such a garment will be to an athlete and without such fit, the therapeutic effectiveness thereof will remain questionable.

Whether for therapeutic or athletic-type applications, when selecting pre-fabricated compression garments, a person is often left with insufficient information when trying to identify the appropriate compression garment. Such pre-fabricated garments are generally selected using a manufacturer's sizing chart and starting pressure levels that are provided by manufacturers. Pressure ranges for such compression garments can apply to a given range of circumferences. This circumference range is often large, which may make it more difficult to understand the compression provided by the garment, especially beyond an initial distal measurement. An individual consumer may fit into several sizes or have parts of his or her arm that fit into different sizes, especially with an edema-caused lobe or node or in an athlete with extensive muscle formation. As a result, the user may end up with ill-fitting compression garments that, at best, provide limited benefits, and, at worst, can end up causing harm to the user. Nonetheless, such pre-fabricated garments remain the status quo for those seeking lower cost and readily obtainable compression garments.

Further, even if a consumer or clinician has a compression chart with detailed compression information for a particular compression garment design, the fitting of compression garments may still be problematic. It can be difficult to decide upon a size and compression class that will meet all specifications of a particular individual. For example, there may be multiple points on a patient where the garment must meet compression specifications. Specifications can require graduated compression values, meaning that compression must vary by a given amount along the length of a limb, for example. Individuals may also have specific characteristics, such as compression sensitivity and varying degrees of swelling in various limb locations, bony projections, etc., which can create even greater complexity in the selection process. The locations for such body part structural variations will necessarily be specific to the individual.

The true external shape of the body part or body area, called "morphology" herein, being fitted for compression garments will be difficult to reproduce using the standard compression garment fitting method of using a tape measure. Tape measures will only identify differences in body part morphology to the extent that a large number of external measurements are made. Since large variations in body part shape can be seen in short distances along the surface of a body part, the conventional tape measurement method cannot generate a shape for the body part or body area being fitted. As such, many custom fitted compression garments often do not provide the desired amount of compression along the whole of the body part or body area being treated with the compression garment. More recently, three-dimensional imaging of a body part or body area has been proposed, however, such methods have not been found to provide clinically accurate reproductions, as discussed in more detail hereinafter.

Still further, certain persons may be interested in obtaining garments that are specifically sized to fit their bodies. Such "custom-fit" garments have traditionally been available only from tailors or seamstresses, and have accordingly been quite expensive and therefore generally out of reach of the average clothing consumer. Yet further, the lack of regulated sizes in the clothing industry makes it difficult for a person to know whether a particular garment will fit her. This not only makes trying on clothes in a retail establishment time consuming for shoppers, but also makes purchase of clothing online particularly challenging.

There remains a need for improved methods of generating accurate shape information for a patient's body part or body area, where such shape information can be used to diagnose and monitor edema and other conditions in a patient, as well as to provide compression therapy to an athlete. Still further, there remains a need for improvements in the fitting of compression garments for use by a specific patient in need of treatment with compression therapy. Yet further, there remains a need for compression garments that closely match the shape of the body part or body area being fitted with the compression garment. Yet further, there remains a need to obtain a better fit for pre-fabricated compression garments. The present invention provides this and other benefits.

SUMMARY OF THE INVENTION

Aspects of the present disclosure are related to fitting for compression garments via digital imaging of a wearer body part and measurement of body part circumferences and, optionally, lengths therefrom. In one example, among others, a method for selecting a pre-fabricated compression garment comprises selecting, by a computer or a user, a wearer body part for fitting with a compression garment; acquiring digital images of the selected wearer body part; and processing, by the computer, the acquired digital images, wherein the processing comprises generating a first wearer fit location circumference measurement for the wearer body part at a first wearer fit location and, optionally, a length for at least part of the wearer body part. The method further comprises providing dimension information for a plurality of pre-fabricated compression garments configured for the selected wearer body part, wherein: a first circumference measurement for each of the plurality at a first garment fit location and, optionally, a garment length measurement is derived the dimension information; and the first garment fit location is at the same location on the wearer as the first wearer fit location; comparing each of the first derived garment fit location circumference measurements for each of the plurality with the first wearer fit location circumference measurement, and, optionally, the garment length measurement with the length for the wearer body part; and identifying at least one pre-fabricated compression garment having a first garment fit circumference measurement that is closest to the first wearer fit location circumference measurement and, optionally, the garment length measurement that is closest to the wearer body part length.

In one or more aspects of the method, information associated with the identified pre-fabricated compression garment can be provided to a user. The selected wearer body part can be at least part of an arm. The first wearer fit location and the first garment fit location can be at or near the wearer's wrist. The selected wearer body part can be at least part of a leg. The first wearer fit location and the first garment fit location can be at or near the wearer's ankle. In various aspects, the digital images are not acquired by rotation of an imaging device on a path about a fixed axis around the wearer or by rotation of the wearer on a platform. The digital images can be acquired by an operator or a device moving an imaging device around the selected body part or body area of interest digital and an image acquisition report can be presented on a screen that is in operational engagement with the image capture device, and wherein the operation of the imaging device can be controlled remotely. A digital image acquisition report can be monitorable by the operator or by the device substantially in real time during the digital image acquisition step, wherein the image acquisition report can include information received about a three-dimensional reconstruction of the selected body part or body area, and wherein the operator or the device can adjust the digital image acquisition in response to the received information. The compression garment can be in the form of an arm sleeve, wherein the garment can be configured to apply a compression value to the wearer's arm of from 10 to 50 mm Hg. The compression garment can be in the form of a leg sleeve, wherein the garment can be configured to apply a compression value to the wearer's leg of from 10 to 50 mm Hg.

In one or more aspects, the method can further comprise generating a second circumference measurement for the wearer body part at a second wearer fit location; deriving from the provided dimension information a second garment fit location circumference measurement at a second garment fit location for each of the plurality, wherein the second garment fit location is the same on the wearer as the second wearer fit location; comparing each of the second garment fit location circumference measurements with the second wearer fit location circumference measurement; and identifying at least one pre-fabricated compression garment having a second garment fit circumference measurement that is closest to the second wearer fit location circumference measurement. In various aspects, the selected body part can be an arm; and the second wearer fit location and the second garment fit location can be at the wearer's wrist. The selected body part can be a leg; and the second wearer fit location and the second garment fit location can be the same location at or near the wearer's knee. At least two or more wearer fit locations and garment fit locations can be generated for each selected body part. Information associated with the identified pre-fabricated compression garment can be provided to a user. The length of at least part of the body part of interest can be derived from the image processing step.

Further aspects of the present disclosure are related to methods of generating a shape description from digital images for a body part or body area of interest and use of such shape description information. The generated shape description information can be used to make compression garments specifically configured for the body part or body area. Compression garments generated from the shape description information are also included herein.

In one aspect, among others, a method for making a compression garment comprises selecting a body part or body area of interest in a patient in need of compression thereby, the body part or body area having a surface morphology of that patient; acquiring digital images of the selected body part or body area; processing the digital images by a computing device, wherein: the processing of the digital images comprises generating shape description information for the selected body part or body area; the generated shape description information comprises geometric information for the selected body part or body area, the geometric information associated with the surface morphology of the selected body part or body area of the patient; and measurement information for the selected body part or body area can optionally be derived from the shape description information; providing at least one compression value identified as therapeutically appropriate to provide compression therapy to the patient when the at least one compression value is incorporated into a compression garment fabricated from the shape description information or the optional measurement information; and fabricating the compression garment from the shape description information or the optional measurement information, wherein the fabricated compression garment incorporates the provided compression value. In one or more aspects, the selected body part or body area can be at least part of one arm or at least part of one leg. The digital images can be acquired by an operator moving an imaging device around the selected body part or body area of interest. The imaging device can be free to move around the selected body part or body area with six degrees of freedom, unconstrained by a mounting or support assembly. In various aspects, the digital images may not be acquired by rotation of an imaging device on a path about a fixed axis around the patient or by rotation of the patient on a platform.

In one or more aspects, the operator can observe a digital image acquisition report in substantially real time during the digital image acquisition step, wherein the image acquisition report includes information about a three-dimensional reconstruction of the selected body part or body area, and wherein the operator can adjust the digital image acquisition in response to the received information. The digital image acquisition report can be presented to the operator on a screen that is in operational engagement with the image capture device. The selected body part or body area can comprise at least one knob or lobe, the surface morphology of the patient thereby having a complex surface morphology for the body part or body area. In various aspects, the compression garment can be in the form of an arm sleeve, wherein the provided compression value is from about 20 to about 50 mm Hg, wherein the compression is incorporated in an area distal from a top end of the sleeve, and wherein the top end is proximal to either an elbow area or a shoulder area on the patient. The compression garment can comprise geometric features associated with a bony area of the selected body part or body area identified by the shape description information. In some aspects, the at least one compression value comprises graduated compression values incorporated from a distal end of the fabricated compression garment.

The identified embodiments and aspects are exemplary only and are therefore non-limiting. The details of one or more non-limiting embodiments of the invention are set forth in the accompanying drawings and the descriptions below. Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

DETAILED DESCRIPTION OF THE INVENTION

Figure 4:
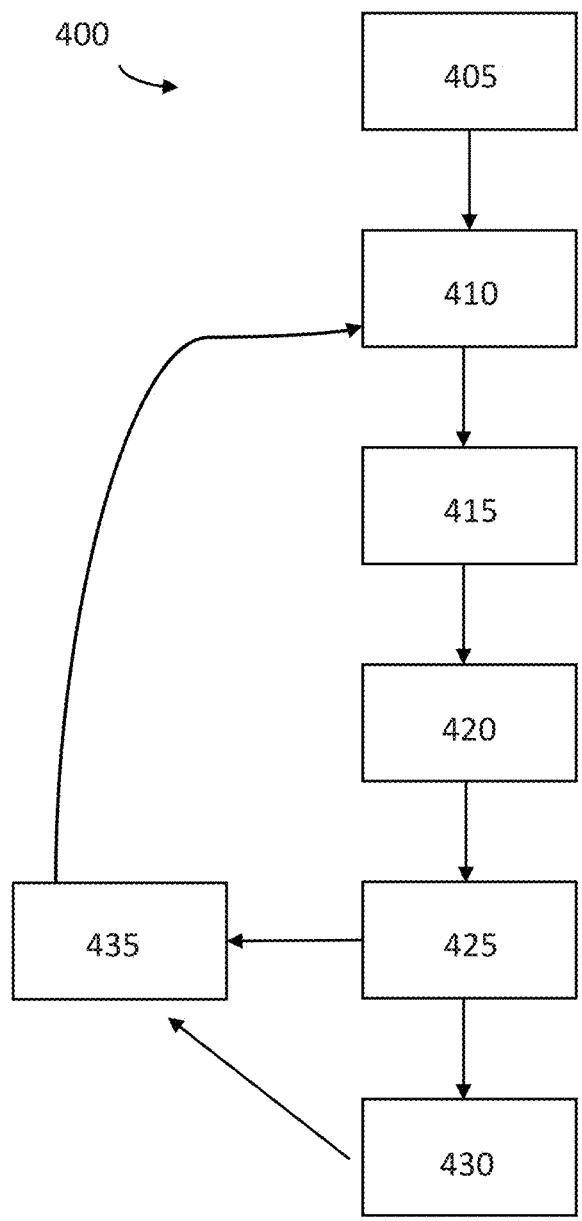

FIG. 4 provides an overview of a process of the present invention.

Figure 5:
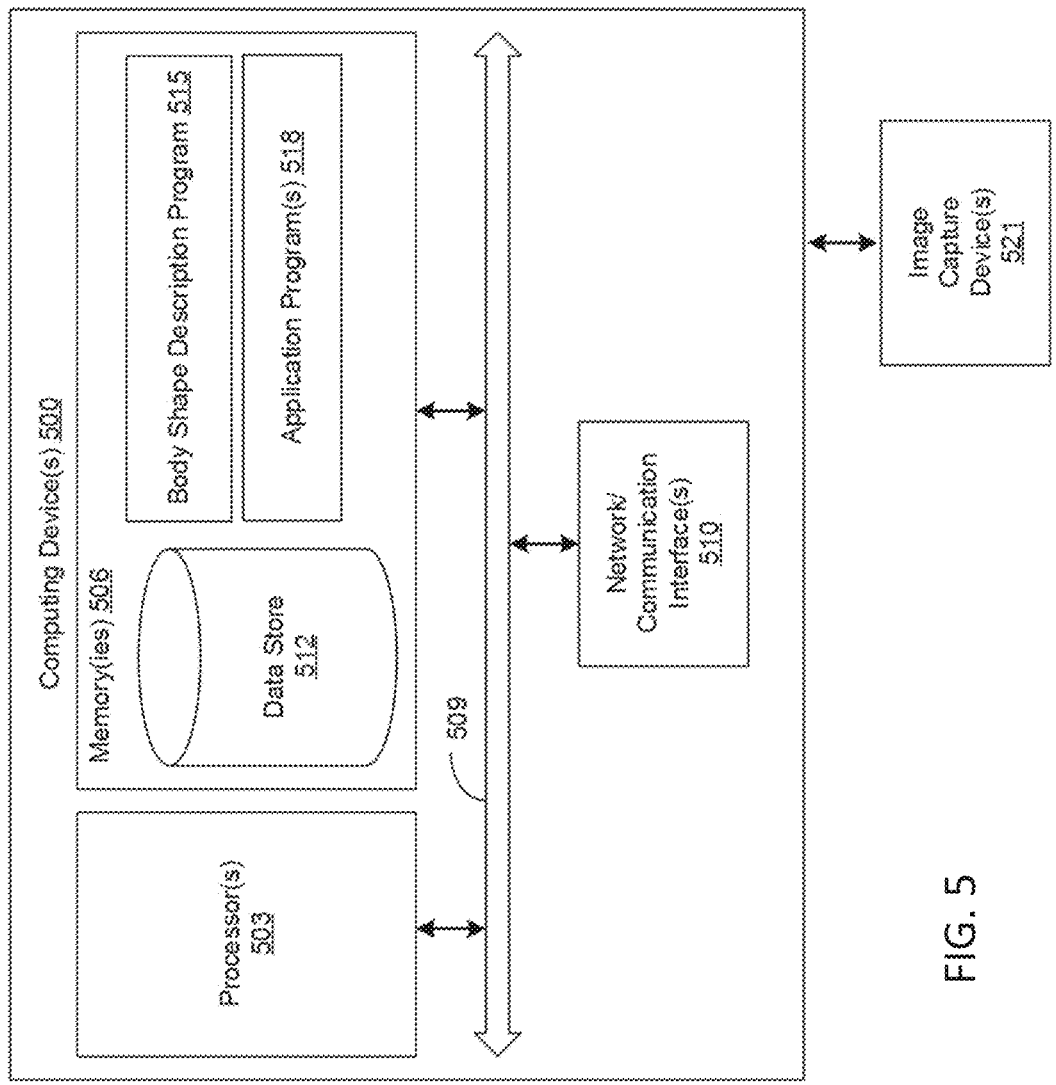

FIG. 5 is a schematic diagram illustrating an example of a computing system for implementing body shape description and measurement, in accordance with various embodiments of the present disclosure.

Figure 6:
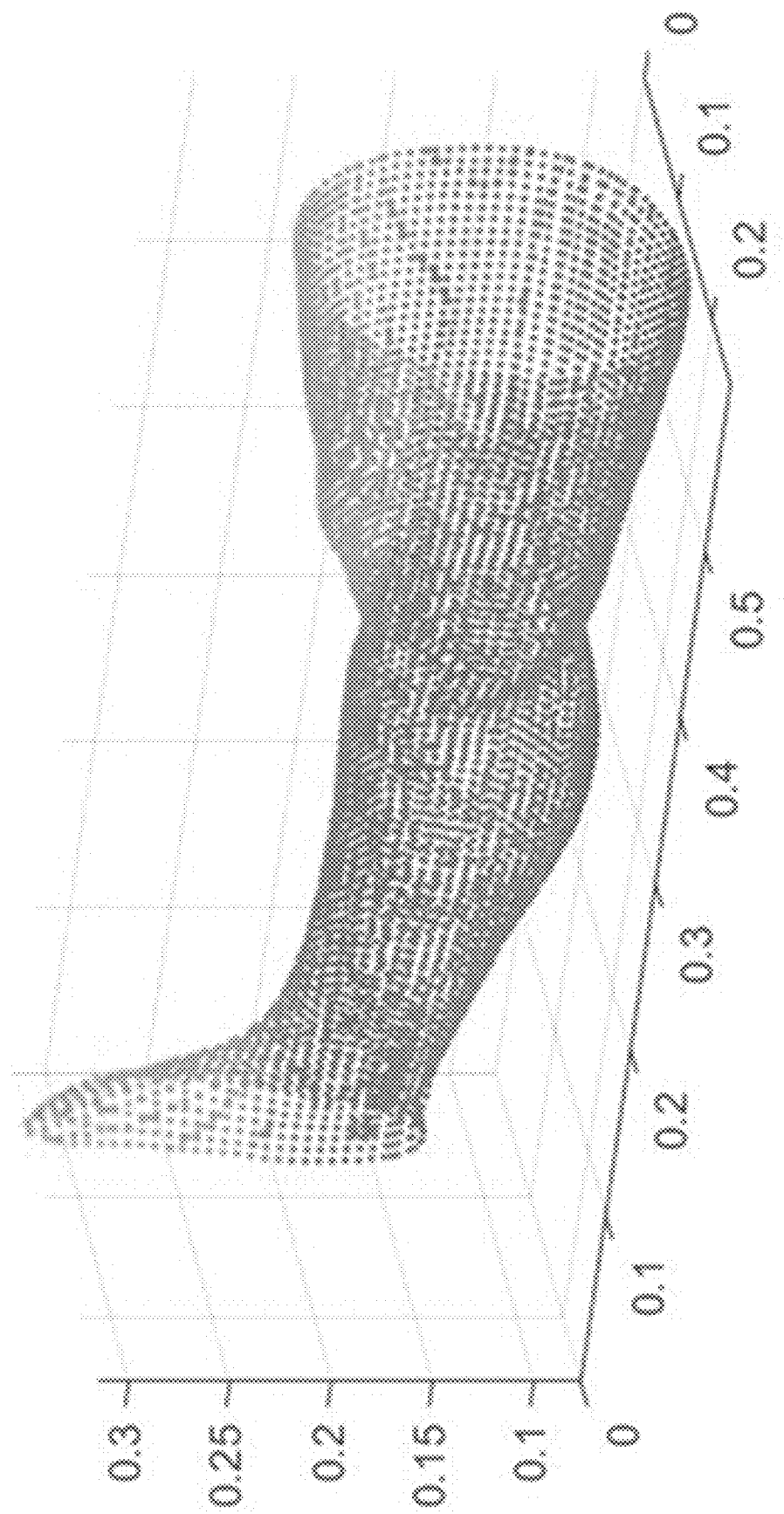

FIG. 6 illustrates a point cloud generated from a plurality of digital images of a patient's leg, where a shape description and measurement information can be derived therefrom.

Figure 7:
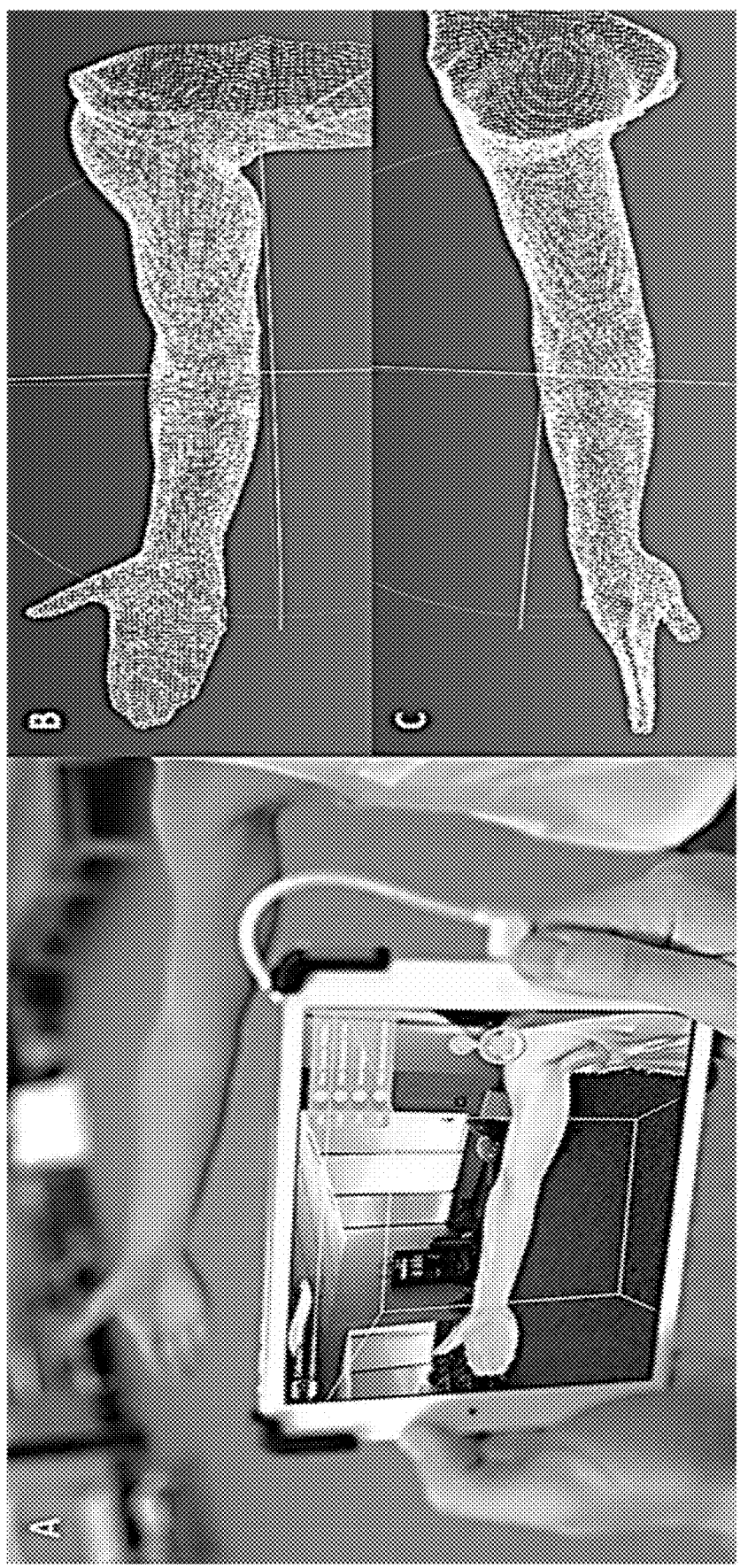

FIG. 7 shows part of an image acquisition technique for a handheld technique.

Figure 8:
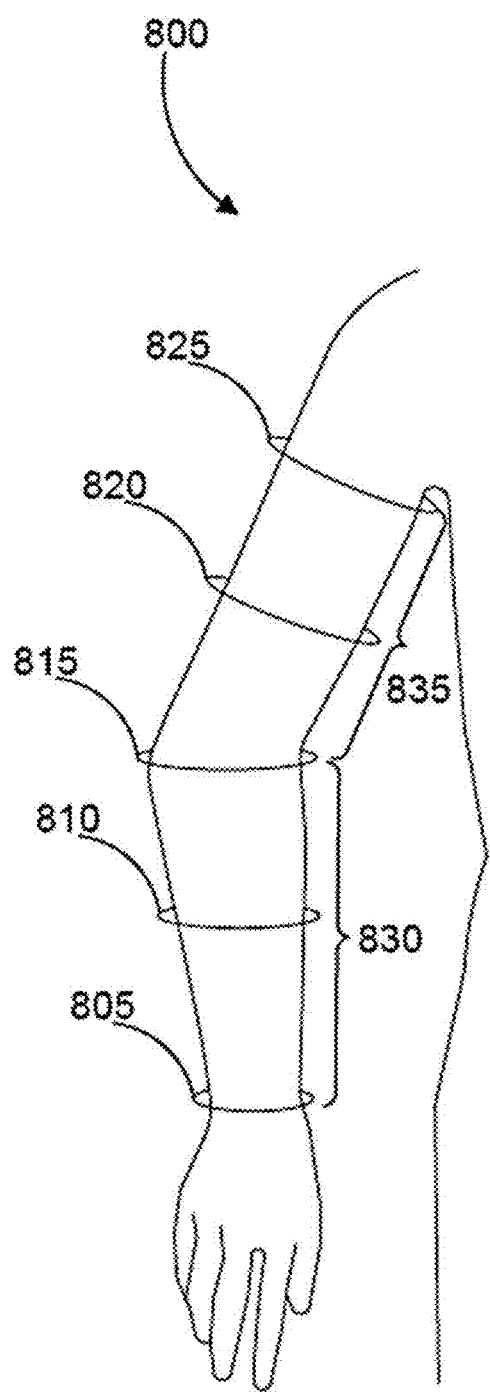

FIG. 8 is a diagram of an arm showing exemplary measurement points for fitting of a compression garment.

Figure 9:
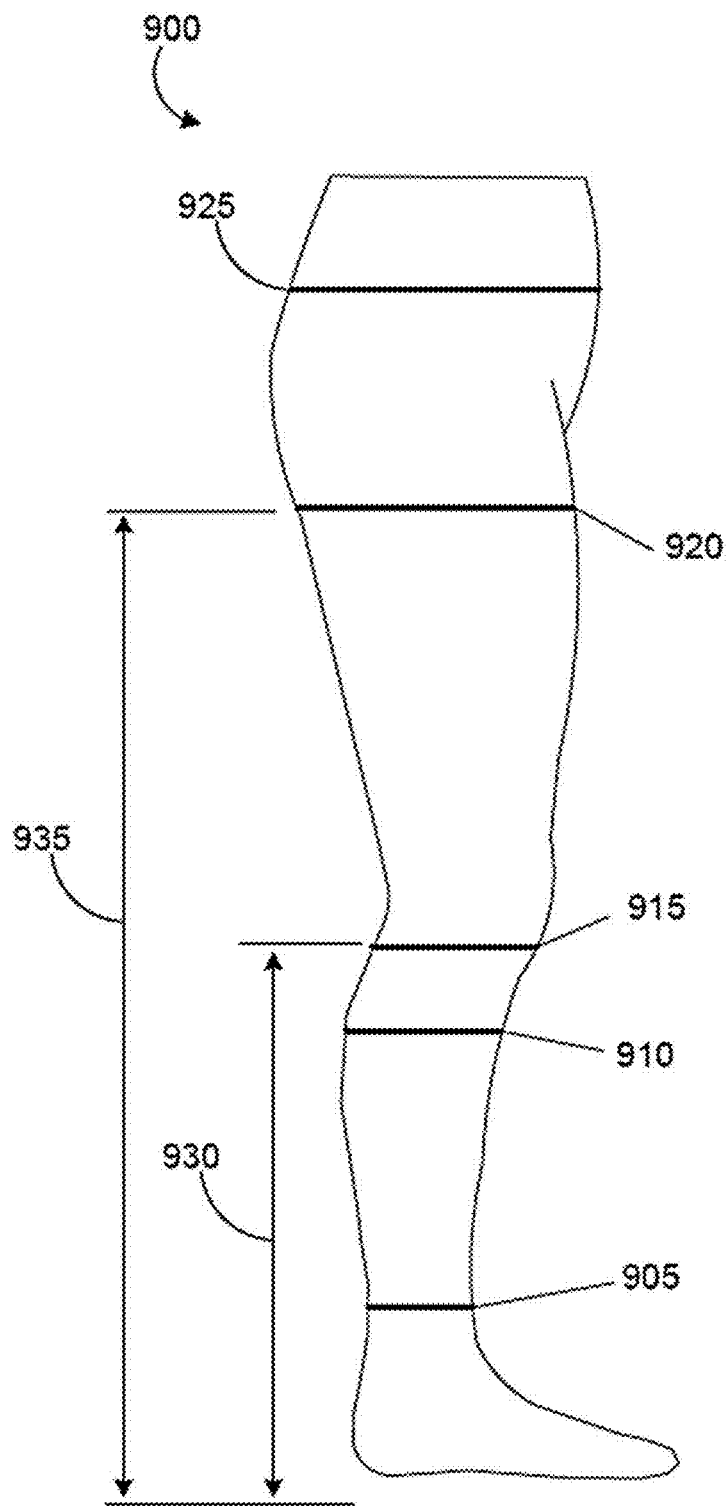

FIG. 9 is a diagram of a leg showing exemplary measurement points for fitting of a compression garment.

Figure 10:
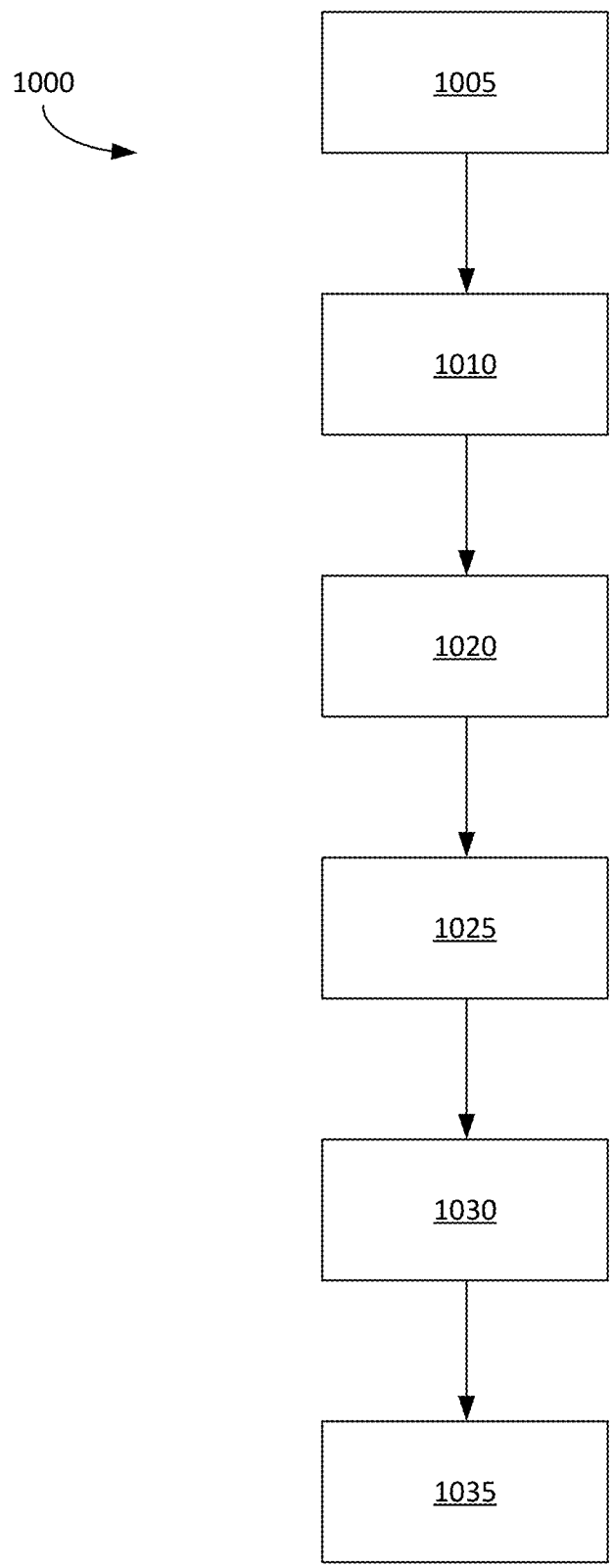

FIG. 10 is a diagram illustrating an example of a process for fitting a pre-fabricated compression garment for a wearer.

DETAILED DESCRIPTION OF THE INVENTION

In the following detailed description, reference is made to the accompanying drawings, which form a part hereof, and within which are shown by way of illustration certain embodiments by which the subject matter of this disclosure may be practiced. It is to be understood that other embodiments may be utilized and structural changes may be made without departing from the scope of the disclosure. In other words, illustrative embodiments and aspects are described below. But it will of course be appreciated that in the development of any such actual embodiment, numerous implementation-specific decisions must be made to achieve the developers' specific goals, such as compliance with system-related and business-related constraints, which may vary from one implementation to another. Moreover, it will be appreciated that such development effort might be complex and time-consuming, but would nevertheless be a routine undertaking for those of ordinary skill in the art having the benefit of this disclosure.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Where ever the phrases "for example," "such as," "including" and the like are used herein, the phrase "and without limitation" is understood to follow unless explicitly stated otherwise.

The terms "comprising" and "including" and "involving" (and similarly "comprises" and "includes" and "involves") are used interchangeably and mean the same thing. Specifically, each of the terms is defined consistent with the common United States patent law definition of "comprising" and is therefore interpreted to be an open term meaning "at least the following" and is also interpreted not to exclude additional features, limitations, aspects, etc.

The term "consisting essentially of" is meant to exclude any features that would change the basic and novel characteristics of the present invention, as claimed.

The term "about" is meant to account for variations due to experimental error. All measurements or numbers are implicitly understood to be modified by the word about, even if the measurement or number is not explicitly modified by the word about.

The term "substantially" (or alternatively "effectively") is meant to permit deviations from the descriptive term that don't negatively impact the intended purpose. Descriptive terms are implicitly understood to be modified by the word substantially, even if the term is not explicitly modified by the word substantially.

"Edema" is the accumulation of excess fluid in a fluid compartment. This accumulation can occur in the cells (i.e., cellular edema), in the intercellular spaces within tissue (i.e., interstitial edema), or in other spaces in the body. Edema can be caused by a variety of factors, including indications associated with osmotic pressure, such as ashypotonic fluid overload, which allows the movement of water into the intracellular space, or hypoproteinemia, which decreases the concentration of plasma proteins and permits the passage of fluid out of the blood vessels in to the tissue spaces. Other factors can include poor lymphatic drainage (known as "lymphedema"), conditions associated with an increased capillary pressure (e.g., excessive retention of salt and/or water), heart failure, and conditions associated with increased capillary pressure, such as inflammation (e.g., burns or other trauma).

As used herein, the phrase "detecting edema" or "diagnosing edema" means detecting or diagnosing the existence of edema, as well as the onset of edema, early stage edema and the progression of edema over time. Thus, methods for detecting edema can also be used to monitor the progression of edema over time and treat/manage edema in an individual.

The term "lymphedema" may include either primary or secondary lymphedema, the latter of which might also be term "acquired" lymphedema. Some forms of lymphedema can occur in morbidly obese patients, such as the condition known clinically as "Massively Localized Lymphedema." Lymphedema is a category of edema, although it is also characterized as a separately treatable indication, such as when it is a complication of breast cancer treatments in which lymph activity in patients is affected. As would be recognized, primary lymphedema is caused by abnormal development of the lymph system. Symptoms can be present at birth, or may appear later in life. Secondary lymphedema is caused by damage to the lymphatic system. The lymphatic system may be disrupted, damaged or blocked by infection, injury, cancer, removal of lymph nodes, radiation to the affected area or scar tissue from radiation therapy or surgery. In some aspects, the present invention provides methods of detection of lymphedema that occurs as a result of removal or damage to lymph nodes that occurs after treatment of a patient for breast cancer.

"Post-recovery compression treatment" means the application of compression therapy via wearing of a garment providing one or more compression values to at least one area on a person after an exercise event. The types of exercise events are expansive and can, for example, include running/jogging/walking, weight lifting, swimming, participation in team sports (e.g., football, basketball, soccer, baseball), and the like.

"Compression garment" as used herein means garments that are constructed from elastic material and that are intended to apply pressure when stretched over the skin while being worn. Compression garments are worn over an area of the body where a therapeutic response (e.g., for treatment of lymphedema or swelling post-surgery etc.) or, when used in sports-related applications, for post-recovery compression treatment for enhanced recovery of a person after an athletic event. Typically, compression garments comprise one or more compression values that, when worn by a patient in need of treatment, are configured to apply an intended or prescribed level of compression therapy to the patient. When a person is wearing compression garments that are properly sized and fitted for that person's limb, trunk or extremity, etc., such garments apply a pressure to the skin that is generally dependent on both the material construction and the size and the shape of the garment, and how well the garment conforms to the unique aspects of the wearer's shape. An intended or prescribed level of compression therapy for a patient in need of treatment is the selection of one or more compression values to be applied to the patient during the wearing of a compression garment.

"Anthropometry" means the measurement of the size and proportions of the human body. "Anthropometric measurements" are measurements that comprise information regarding the contour, volume, overall size and other relevant information, where such information has relevance to the fitting of garments that are specifically sized for a person in need of fitting for such garments.

In broad constructs, the present invention provides advancements in generation of mathematically accurate information about the shape of a body part or body area in a person or, if in a medical context, a patient. A patient can be a human or an animal. In some aspects, the inventive methodologies herein provide improvements in the ability to detect edema and other conditions associated with swelling of a body part or body part area, as well as being useful in generating compression garments from such mathematically accurate information, where such compression garments are derived from imaging of such body part or body part areas.

The inventive enhancements can be attributed to, at least in part, the incorporation of shape description techniques to derive accurate numerical information about the shape of the body part or body area of interest in a three-dimensional coordinate system, wherein shape comprises geometric—that is, numerically based—information that is invariant to translation, rotation, and scaling.

Such numerically based shape information is to be distinguished from prior art imaging techniques for body part and body areas where a shape representation is derived therefrom. Shape representation methods result in a non-numeric representation of the original shape (e.g., a graphical representation), where certain aspects of the shape are preserved, so that the shape can be processed from that representation. Accurate geometry—that is, mathematical information—is not directly derivable from a shape representation. In other words, the measurements of the subject object, such as a body part or body area in the present invention, can only be approximated or determined indirectly by using a reference scale using shape representation methodology. Such measurements require generation of an accurate and scale invariant reference scale in order to have utility.

In contrast, a shape description results from a processing step subsequent to shape representation, whereby the unique aspects of the shape of the object in the image can be derived accurately in geometric/numerical form. In this regard, accurate numerical information about one or more unique features of the shape of interest—here a body part or body part area—are derivable from the plurality of acquired digital images.

Specifically, in the context of the enhancements possible with the present methodology, a person or patient's unique body part or body area surface morphology characteristics are derivable herein. Such surface morphologies are provided by the generation of a shape description for the selected body part or body part area that are derived from shape analysis techniques known to those of skill in the art.

In one aspect, the Laplace-Beltrami equation:

$$\Delta u = \frac{\partial}{\partial \xi}\left(\frac{F\frac{\partial u}{\partial \eta} - G\frac{\partial u}{\partial \xi}}{\sqrt{EG - F^2}}\right) + \frac{\partial}{\partial \eta}\left(\frac{F\frac{\partial u}{\partial \xi} - E\frac{\partial u}{\partial \eta}}{\sqrt{EG - F^2}}\right) = 0.$$

can be used to resolve the shapes of the body part or body area of interest. Still further, Fourier Descriptors or Turning Functions can be used as discussed in R. C. Gonzalez and R. E. Woods, *Digital Image Processing*, Englewood Cliffs, N.J.: Prentice Hall, 2007, and Volotäo, Carlos F S, et al., "Shape characterization with turning functions," *Proceedings of the 17th international conference on systems, signals and image processing*, Editora da Universidade Federal Fluminense, Vol. 1, 2010, respectively. Still further, the alpha-shape family of algorithms, as first introduced in H. Edelsbrunner, D. G. Kirckpatrick, and R. Seidel, "On the shape of a set of points in a plane," *IEEE Transactions on Information Theory*. Vol. 29, Issue 4, 1983, which is derived from the Delaunay Triangulation, can be used to define shape and shape boundaries in two and three dimensions, for example such that the boundary is defined as $\partial S_\alpha = \{\Delta_T | T \subset S, |T| \leq d,$ and $\Delta_T$ is $\alpha$–exposed$\}$. The disclosures of these references are incorporated herein in their entireties by this reference.

The inventive methodology can generate shape description information about one or a plurality of patient areas along a body part or body areas, such as all or part of a leg, an arm, neck, torso etc., where such shape description information can be utilized in assessing the amount of swelling on a specific person on a longitudinal basis, such as from day to day, week to week, month to month, and year to year, for example.

In their work with patients symptomatic of edema, the inventors herein have determined that existing three-dimensional digital imaging of body part and body areas for analysis, while generating depth maps and the associated point clouds for analysis, nonetheless do not provide suitably accurate clinical results. All of the reviewed prior art imaging methodology intentionally reduce the complexity of the generated point clouds so as to generate measurements of the body part or body area of interest. For example, isobar Compression, a company that generates compression garments from digital imaging (see http://www.isobar-compression.com/) specifically refers to down-sampling the point cloud to generate transverse cross-sectional measurements with limited metric extraction (circumference, radius of curvature, etc.). Said differently, all prior art methods known to the inventors herein discretizes the point cloud to provide simple one and two-dimensional measurements.

The reason for all prior art simplifying the measurement process is believed by the inventors herein to: (1) address the mathematical complexity involved in generating more advanced geometric information (i.e., it is not a trivial step to progress from simple one or two dimensional cross-sectional measurements to detailed shape description in 3 dimensions); and (2) a lack of knowledge of the need and value of geometric analysis in diagnosing conditions and/or designing garments for patients in need of treatment with compression therapy, as provided by the inventors herein.

As to the latter, the inventors herein have discovered that accurate diagnosis and monitoring of edema-like conditions can be enhanced with use of the methodology herein. Yet further, the inventors have found that determination of the sizing and fit of compression garments—both custom and pre-fabricated—can be greatly improved by generation of three-dimensional geometric information from the digital images by way of the generated point clouds.

Moreover, the inventive image acquisition processes suitably generate point cloud information that is optimizable to generate geometric information that is relevant to patients with edema and similar conditions, which is a specific clinical insight of the inventors herein.

The quality of prior art body part or body area measurement information was also believed constrained by the use of a discrete set of elements associated with the body part or body area of interest, namely, length, circumference at defined intervals, which were used to generate measurement information that could not resolve the unique surface morphological features associable with a specific patient's body part or body area. Such prior art measurement techniques have been found by the inventors herein to not allow the generation of fully accurate, geometrically-based, 3D representations of a patient's body part or body part area, at least in regard to unique surface morphologies for that patient. This, in turn, was found to limit the diagnostic and therapeutic effectiveness of the measurement information so obtained.

Prior art methodology generally uses a series of "stacked" cross-sections to represent a limb, for example, as cross-sectional "slices" provided in a defined thickness interval (e.g., mm, cm, etc.) Using these prior art models, the geometry of a limb, for example, is therefore only understood in a series of transverse sections, that are "generically" reconstructed to provide information substantially without characterization of unique morphological features of that patient. The inventors herein have determined after extensive analysis that such prior art methodologies do not comprise enough information about the subject body part or body part area for some relevant use cases.

In some aspects, the inventive methodology includes axial measurements to generate the shape description, and associated information. Such axial measurements can be in the form of surface lines substantially spanning the length of the patient body part or body area of interest. Such surface lines can be spaced at a degree δ around the body part or body area of interest. The inventive methodology can therefore be conducted in multiple planes and in multiple dimensions to allow acquisition of a shape description which, in turn, results in higher quality measurement information for analysis and use.

As an illustrative example, consider a patient who exhibits swelling on the outer side of her forearm. Using a prior art methodology, a volume-based measurement (that is, methodology that considers arm geometry to be an approximation of a cylinder) would indicate that there is swelling in the forearm, but information about the precise location of such swelling would be absent. Analysis of circumference measurements could indicate that swelling was occurring in the forearm, but not which side of the forearm the swelling was presenting. Radius of curvature information could indicate that the forearm has more of less curvature along the length thereof, but information about the precise degree of curvature would be lacking. Circumference would indicate that forearm swelling has gone down and upper arm swelling has gone up but no information about which side of the arm the swelling was presenting.

In contrast, shape description and the mathematically accurate information derivable therefrom, such as provided with the inventive methodology, can provide a markedly higher degree of detail as to the exact location of swelling on the forearm on a specific patient, as well as the size thereof. The present invention allows the unique surface morphology of a specific patient to be resolved from digital imaging of a body part or body area on that person. Shape description and associated mathematically accurate information derivable from digital imaging conducted over time can also provide the exact degree to which the shape characteristics of this patient's forearm and on her upper arm have changed, which would further inform ongoing treatment of this patient and to allow compression garments fitted to the specific morphological characteristics of this patient to be appropriately fabricated. In this regard, the inventive methodology has been found to generate enhanced geometric information about the forearm and any morphologies thereon, such as the "bump" indicated by swelling. In other words, the use of shape description allows one to determine not only that the bump is present and its size on this patient, but also where the bump is positioned in three-dimensional space, which is determined based upon shape description of the surface boundary.

In further aspects, the enhanced measurement information derived from an imaged body part or body part area has been found to enable improved diagnosis and monitoring capability, as well as allowing generation of therapeutic direction for that patient. Such enhanced information has been found to be highly relevant to understanding changes in the swelling of a specific patient's limb or a body part over a time period, and to generate a well-fitting compression garment that suitably applies a prescribed level of compression therapy.

Turning back to the example of the patient with a bump on her forearm, a prescribed therapy, such as massage therapy, could result in the bump moving to another location on her arm, perhaps as far away as the upper arm. Without use of the inventive technique that applies shape description to generate precise information about the surface morphology of the specific patient at each imaging event from which shape description information is obtained, knowledge about the effectiveness (or lack thereof) of the prescribed treatment would be lacking if the imaging technique only reported a volume measurement, as is the case with prior art measurement techniques. This would be an incorrect clinical determination. In contrast, the inventive information derived from shape description techniques would instead return detail about not only about the movement of the swelling within the arm, but also its size and location on the arm, thus allowing, among other things, a clinical assessment that takes into consideration the effect of the prescribed treatment, massage therapy in this example. This can allow a clinician or other medical provider to generate a treatment plan based on actual knowledge of the effects of an applied treatment, including compression therapy as discussed elsewhere herein.

It has been found that a first highly accurate three-dimensional depiction of a patient's specific body part or body area shape or morphology, such as is possible with the shape descriptions herein, can serve as a baseline for monitoring of subsequent changes in that same body part or body area morphology, thereby providing predictive insight as to ongoing symptoms of a patient with actual or potential edema.

It has also been found that information about a specific patient's surface morphology as is derivable with shape descriptions for a body part or body part area can be especially useful when generating information in patients having complex surface morphologies, such as those with nodes or lobes on their body surfaces, for example, as occurs with people with high levels of edema and/or who might be morbidly obese. Further, such surface morphology information has been found to be useful in the selection of compression therapy and associated garments for post-exercise recovery.

Notably, people who are symptomatic of edema may also be obese. Patients with complex surface morphologies are often the hardest patients to diagnose for edema and similar conditions due to their highly irregular body part or body area shapes. When using prior art imaging methodologies in the detection of the potential progression of edema, the complex surface morphologies of such patients have been found to greatly reduce the effectiveness of detection. Acquisition of geometric information associated with the specific patient's body part or body area of interest is possible with generation of a surface description that can be used to generate measurement information for the patient's body part or body area of interest has been found to greatly improve the quality of clinical information available for that patient.

With the present invention, diagnosis and monitoring ability is improved over prior art imaging methodology for at least these patients. Moreover, the ability to generate well-fitting compression garments or to enhance the selection of pre-fabricated garments that are intended to deliver a prescribed one or more compression values to a patient having complex surface morphologies is greatly enhanced, at least because the provided garment is custom generated for or selected to fit the specific body part or body area of that patient, even in view of her non-uniform skin surface configuration.

Beyond the specific subset of patients having complex surface morphologies, the inventors herein have determined that measurement of body parts or body areas using the standard tape measure technique or prior art imaging methodology cannot suitably generate a compression garment fit that substantially conforms to the shape of the patient's body part that is in need of compression treatment as is indicated by a compression prescription generated by a provider or as needed by an athlete for post-exercise recovery. In this regard, it has been determined that circumference measurements taken by the tape measurement technique do not provide accurate information about the shape of the parts, and subparts, of the body regions being measured for fitting with compression garments. Moreover, prior art imaging techniques are configured to extract the circumferences of the body parts or body areas of interest. When a body part or body area are assumed to be a circle, which is the case with measurements of body parts or body areas taken according to these prior art methods, a circle, an ellipse, and a square may each demonstrate the same "circumference," but, as would be recognized, would present markedly different shapes.

Figure 1:
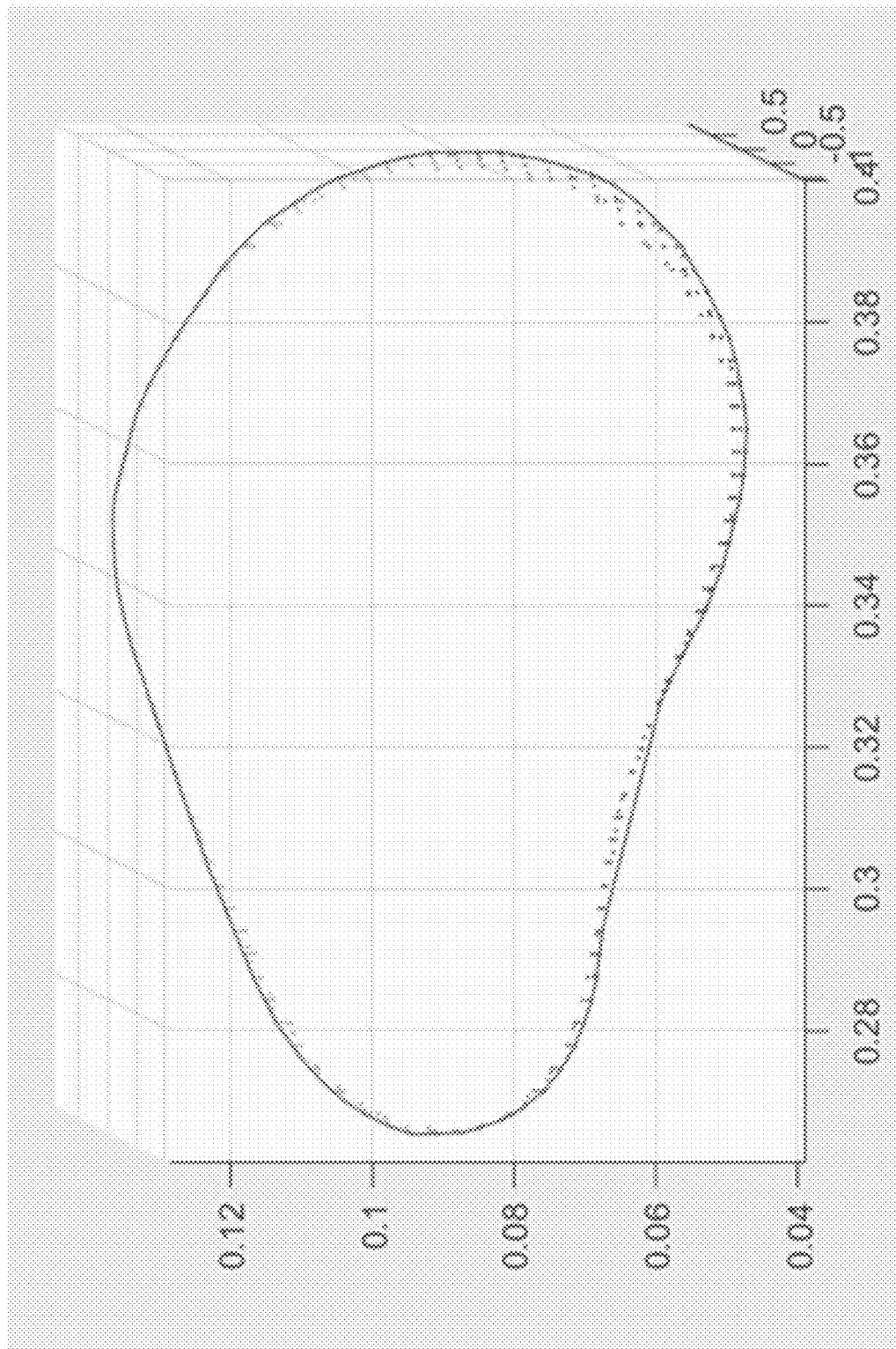
FIG. 1 illustrates a non-circular cross-section indicative of an arm.

Prior art compression garments generated from measurements for the preparation of custom compression garments or for selection of pre-fabricated compression garments using to the prior art methodology are fitted according to the premise that the body part being fitted essentially has a circular cross section, even while the person's arm or leg (or other body part) may, in fact, deviate substantially from a circle along the length thereof. The inventors have determined that the flawed assumption of a circular cross-section can, in turn, distort the pressure applied to the body part to which compression therapy is being applied. Such distorted pressure will result in a deviation in all or part of the intended compression values and compression gradients being applied to the body part by the compression garment. Accordingly, the compression effectiveness of the compression garment generated from only a plurality of circumferential and length measurements taken by a tape measure when the patient's body part being treated with compression deviates from the assumed cylindrical cross section. FIG. 1 shows an example of a non-circular cross-section of an arm.

With specific reference to prior art three-dimensional digital imaging of body part and body areas for analysis of lymphedema, all such digital imaging methods reviewed by the inventors herein generate point clouds for analysis. However, all of these prior art methods intentionally reduce the complexity of the point cloud in order to extract measurements of the body part or body area of interest. For example, Isobar Compression, a company that generates compression garments from digital imaging (see http//www.isobar-compression.com/) specifically refers to downsampling the point cloud to generate transverse cross-sectional measurements with limited metric extraction (circumference, radius of curvature, etc.). Said differently, all reviewed prior art discretizes the point cloud to simple one and two-dimensional measurements.

Further with regard to the clinical realization, the inventors herein have discovered that accurate diagnosis and monitoring of edema, and other conditions, as well as the sizing and fit of compression garments specifically configured for the person such as an athlete in need of post-exercise compression therapy, can be greatly improved by generation of three-dimensional geometric information from the digital images by way of the generated point clouds. Moreover, the inventive image acquisition processes suitably generate point cloud information that is optimizable to generate geometric information that is relevant to patients with edema and similar conditions, which is a specific clinical insight of the inventors herein.

Yet further, the use of shape description information that is highly accurate as to a specific person has been determined by the inventors herein to allow the addition of features such as mobility regions for elbows and knees that, when included in a compression garment derived from such measurement information, has been found to improve fit and patient compliance. In this regard, areas of the patient having specific morphological characteristics (e.g., curves, bends, sharpness, etc.) can be substantially identified and incorporated into shape descriptions and associated information according to the methodology herein, and a compression garment generated that is substantially matched to the patient's precise surface morphology can be generated. Incorporation of such patient specific surface morphology into a compression garment, such as geometric features associated with bony areas on the patient's elbow, can reduce the propensity of the compression garment to cause friction sores on the patient during wearing thereof, for example. In addition, the compression garment can include non-compressive materials or openings at bony areas or joints to reduce or eliminate pain, irritation or restriction of movement. These can be identified by the morphological characteristics of the shape descriptions.

Figure 2:
FIG. 2 illustrates images of a patient with Stage 3 lymphedema on a lower leg.

Moreover, the inventors herein have found that with better fitting compression garments and compression garments having shapes that more closely match those of the body part or body area of interest, resultant pressures applied from the garment will be much closer to the pressure prescribed by the clinicians, which is expected to result in improvements in therapeutic outcomes. For example, a clinical condition of "massively localized lymphedema," is occurring in greater frequency in persons who are morbidly obese. Such patients typical present clinically with a large fold or lobe extending from an upper area of the thigh to extend typically down to the knee area Compression therapy is often indicated for such patients, however, the complex surface morphology results in a difficult fitting procedure that can result in a compression garment that likely only approximates the shape of the patient area being treated. Using the imaging methodology of the present invention, digital images can be processed to derive a shape description of the patient's body part or body area—here the patient's upper leg region— which can be rendered into measurement information that substantially matches the unique surface morphology of the patient to thereby allow highly customized compression garments to be obtained. Such processing incorporates a step of "stitching" or "fusing" of the digital images together, so as to derive the shape description. FIG. 2 shows a further example of a complex patient surface morphology resulting from a lower leg stage 3 lymphedema presentation.

In further aspects, the methodology herein allows compression garments to be generated, wherein the compression garments are substantially matched to the surface morphology of an individual person, in other words, the garments are customized for the person in need of compression therapy. As would be recognized, compression therapy is indicated for conditions involving venous and lymphatic insufficiency in the lower limbs, including varicosities, lymphedema, venous eczema and ulceration, burn treatments, deep vein thrombosis and post-thrombotic syndrome, among others. A person, for example, a patient with actual or potential symptoms of edema or the like, can be imaged along at least part of one body part or body part area of interest to generate digital images of the body part or body area of interest that can be rendered into shape descriptions and associated information derivable therefrom that is substantially matched to the specific patient's body part or body part area.

Compression garment fit parameters are defined for a patient by a provider or using prescribed compression information. Compression garments are configured to apply more pressure distally while gradually decreasing pressure as the garment travels up the extremity. Compression helps encourage and facilitate fluid movement for patients affected by lymphatic and venous disorders. With appropriate compression application, vessels in the circulatory and lymphatic systems can absorb more fluid from tissues. The result is increased absorption of tissue fluid and decreased swelling.

Compression garments can be indicated for the lower extremities in the form of leg stockings, such as disclosed in US Patent Application Publication No. 20150051524, the disclosure of which is incorporated herein in its entirety by this reference. The '524 Publication discloses compression stockings in which compressions for therapeutic effect are incorporated therein. Such compression garments can be generated from information obtained according to the inventive methodology herein. Compression garments having prescribed compression values therein can also be indicated for the upper body and arms in the form of compression sleeves for the arm, worn with or without a hand component (e.g., fingerless glove or a gauntlet that does not have individual finder openings), or a support bra for the chest area or a vest for the entire trunk area.

Figure 3:
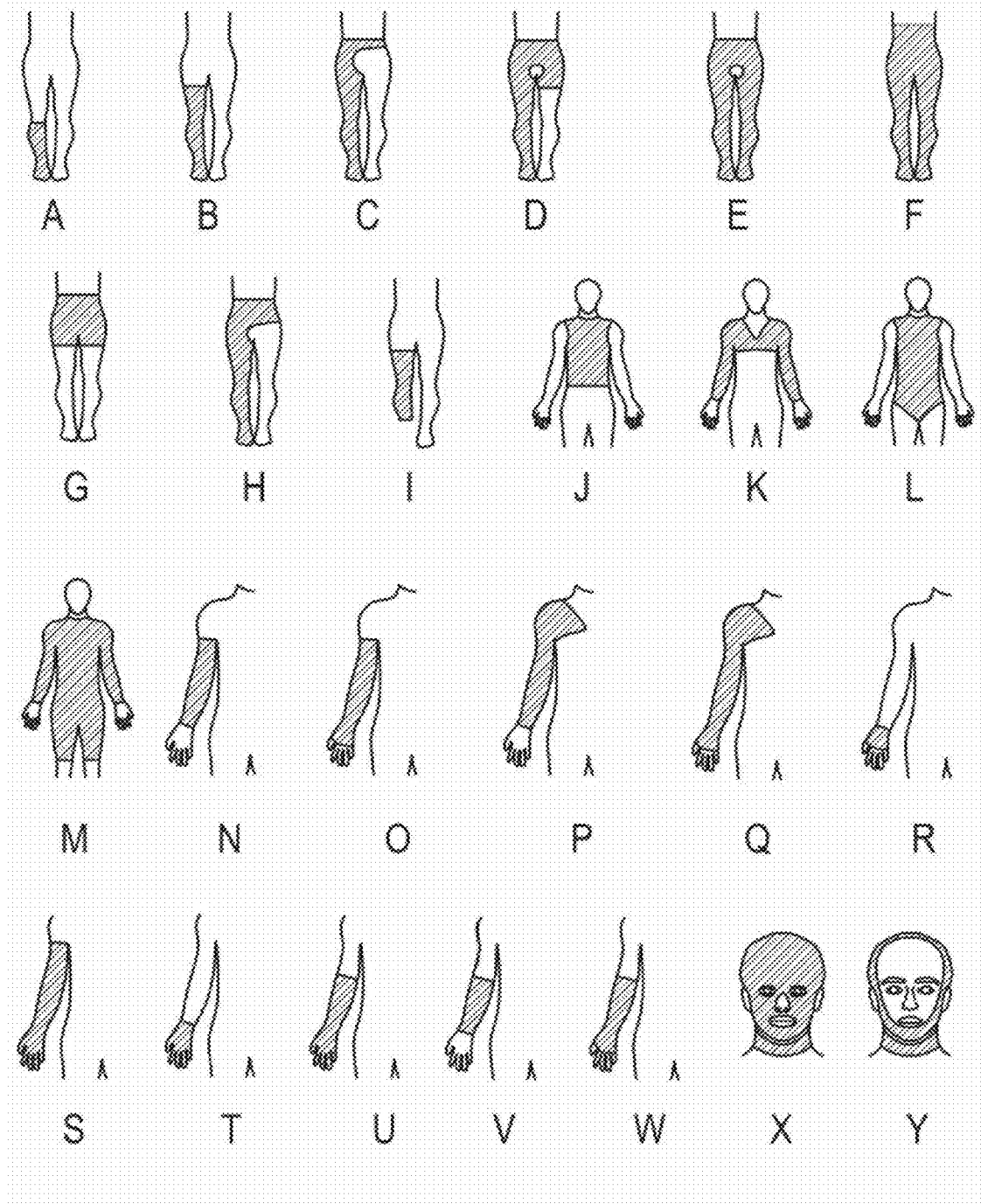
FIG. 3 illustrates a collection of compression garment configurations that can be generated with the methodology of the present invention.

A variety of compression garment configurations are derivable from the methodologies herein. Such configurations include, but are not limited to those illustrated in FIG. 3. Other variations can also be generated, as indicated by the patient's medical condition or post-exercise recovery need. In order to suitably generate such compression garments having a prescribed or indicated compression prescription incorporated therein for a patient in need of treatment, the methodology herein can be used to obtain measurement information derived from shape descriptions generated from imaging of the body part or body area of interest as discussed further herein. Fabrication instructions can be generated from such measurement information. Still further, generated shape descriptions can be used to generate suitable fabrication instructions.

cause fluid backup to worsen. The specific external pressure applied to the body part or body area can also exert a massaging effect on the body part or body area to enhance the therapeutic action of a compression garment.

The inventors herein have found that prior art measurement information—whether derived from measuring the patient directly such as by a tape measure or that is derived from prior art image acquisition techniques—used to generate custom fitted compression garments do not adequately take into account the unique shapes, that is, surface morphologies of each patient. In this regard, the inventors have determined body part or body area shape description and information derivable therefrom that is derived from shape descriptions obtained from imaging can greatly improve the fit, and therefore, therapeutic efficacy of one or more prescribed compression values in patients in need of compression therapy. Moreover, such shape descriptions and associated derivable information is particularly useful in persons with complex body morphologies, such in people having lobes or folds along the body part or body part area where compression therapy is indicated. Still further, such shape description information can be used to generate fit information for a person in the selection of pre-fabricated—that is, ready-to-wear or off-the-shelf—compression garments as discussed in more detail hereinafter.

TABLE 1

TYPES OF COMPRESSION GARMENTS

| A-knee high stocking one leg | B-thigh high stocking One leg | C-full leg stocking chap style one leg | D-full leg stocking with brief one leg (open crotch shown, but also can be closed crotch) | E-full leg stockings two legs (open crotch shown, but also can be closed crotch) | F-chest high stockings for pregnancy two legs | G-panty girdle (above knee shown, but can also be below knee) |
|---|---|---|---|---|---|---|
| H-one leg open crotch with high leg brief | I-stump stocking (below knee shown, but also can be above knee) | J-torso shirt (no sleeves shown, but can also have sleeves) | K-two arm half shirt (two arms shown, but can also be one arm) | L-short bodysuit (no sleeves shown, but can also be with one or two sleeves) | M-long bodysuit (sleeves shown but can be no sleeves) | N-wrist to axilla gauntlet |
| O-metacarpals to axilla gauntlet and glove | P-wrist through shoulder flap gauntlet | Q-metacarpals through shoulder flap gauntlet and glove | R-metacarpals to wrist glove | S-fingers to axilla gauntlet and glove | T-fingers to wrist glove | U-wrist to elbow glove |
| V-elbow to wrist glove | W-metacarpals to elbow gauntlet | X-full face and neck mask | Y-head and neck cover | | | |

As would be understood, compression garments must be properly fitted to achieve the therapeutic results in patients where treatment is clinically indicated or where post-exercise recovery is relevant. In the context of compression therapy in the arm region, at a minimum, an improperly fitted sleeve can reduce the application effectiveness of compression therapy by inadequately applying the prescribed compression s to the patients arm. Moreover, an improperly fitted sleeve can make conditions such as lymphedema worse by placing too much or too little pressure on certain areas of the body part or body part area, which can In some aspects, the present invention comprises obtaining at least one compression value prescribed for a patient from a provider. Such prescription will include at least an identification of the body part or body part area upon which the compression therapy is to be applied via a compression garment and one or more compression levels to be incorporated into the compression garment for use.

Compression values to be applied to a person are typically expressed in mm of mercury (Hg), where such units are in relation to the pressure applied by the pressure garment when worn by a patient. Compression values that may be generated for incorporation into compression garments according to the methodology herein are presented in Table 2:

TABLE 2

SAMPLE COMPRESSION VALUES

| | |
|---|---|
| 10-30 mm Hg | Post-exercise recovery |
| 20-30 mm Hg | Mild varicose veins; arterial insufficiency with venous insufficiency |
| 22-28 mm Hg | Burns-prevention of hypertrophic scars |
| 30-40 mm Hg | Moderate varicose veins; assist fluid return; leg fatigue; stasis dermatitis; post-phlebitic syndrome; post-surgical stripping of sclerosing; post-fracture edema; prophylactic treatment of edema and phlebitis; moderate lymphedema |
| 40-50 mm Hg | Chronic venous insufficiency; severe stasis dermatitis; severe lymphedema; severe chronic venous insufficiency; moderate orthostatic hypotension |
| 50-60 mm Hg | Severe orthostatic hypotension, severe post-thrombosis; intractable edema |

The generated compression value information, such as, but not limited to the ranges set out in Table 2, can be incorporated into compression garment manufacturing processes discussed hereinafter.

As noted previously, the methodology herein can be used to monitor the progression or regression of edema and other conditions in a patient. To generate more accurate detection or diagnosis of the occurrence of edema in a patient in need of detection or diagnosis, a baseline body part or body part area shape description is obtained after acquisition of a plurality of digital images of a body part or body area of interest for a patient. The shape description and/or any geometric information therein or any measurement information derivable therefrom can be compared to subsequent shape description(s) and associated information acquired for that patient to determine whether edema or other conditions have changed for the patient over time. Subsequent digital image acquisitions can be performed at intervals concordant with the medical practitioner's standard of care. In some aspects, the subsequent image acquisitions can be conducted on a daily, weekly or monthly basis. The methodology herein is suitable for addressing potential or actual edema of one or more of the upper extremity, lower extremity, head or neck, chest, head or genital areas, as non-limiting examples.

In further aspects, the methods herein can enhance patient access to regular body part or body area examination for the appearance of edema-related symptoms because the imaging processes herein are simple-to-use in that the image acquisition steps can suitably be operated by only minimally trained individuals, as long as high resolution images including clinically accurate information, that is, shape descriptions, geometric information, and/or measurement information derived therefrom, of the body part or body area of interest. As such, the methodology herein can allow more frequent patient monitoring than is normally possible with existing edema detection and monitoring methodologies. In some aspects, the patient image acquisition step can occur in a location remote from the patient's medical team. For example, the patient imaging step can be conducted in the patient's home or other non-clinical setting.

Imaging devices suitable for use in the present invention can comprise any device suitable for generating digital images from which a shape description of the body part or body area can be derived therefrom. One such device is the Kinect 2® device from Microsoft Corporation, which provides depth maps from the imaging process. Another suitable device is the Structure IO® system that combines a sensor engageable with an iPad® or other mobile device to generate digital images that can be processed to generate suitably detailed numerical information about the body part or body area of interest for use herein. Still further, imaging devices that will increasingly be incorporated into mobile devices can also be used to generate images from which shape descriptions can be generated. The Lenovo Phab2 Pro® is an early example of one of these devices.

The imaging devices can be configurable to generate point clouds directly from the imaging step. In some aspects, the imaging acquisition step can be configured to generate as many depth maps as is required in a particular image acquisition process to be able to generate a suitably information dense final point cloud from which a shape description can be derived therefrom. As an example, one could capture one depth map at every degree of rotation around a leg of a patient and the process can be repeated the process at three different heights, which would generate 1,080 depth maps that are used to generate the point cloud. The number of depth maps derivable from the imaging process is dependent, at least in part, by the frame rate of the capture device and the ability to process a suitable amount of data. The ability to generate a shape description from an imaging step, and the associated geometric and measurement information, is highly influenced by the density of the generated point cloud. For example, a point cloud suitable for generating a shape description for an average leg has about 50,000 unique data points in the point cloud.

To suitably obtain the requisite point cloud data from the image acquisition step, the image capture device can be operationally engaged with a device upon which the image acquisition process can be reviewed substantially in real-time during acquisition of the plurality of images. In this regard, the image capture device is in operational and communications engagement with a second device, where the second device has a screen that can be reviewed by the person, or operator, who is operating the image capture device. Alternatively, a second person, or operator, can be reviewing the image acquisition substantially in real time, to provide instructions to the first operator where to direct the image capture device so as to acquire suitable images for use herein. In some aspects, either or both of the first or second operators can be a person. In separate aspects, the either or both of the first or second operators can be a computer or other computing device. If either or both of the first or second operators are computers, at least some of the image acquisition process can be partially or fully automated. Still further, image processing, and any associated image analysis step configurable to provide an edema or other diagnosis, can be by either or both of a person or a computing device, thereby providing full or partial automation thereof.

In some aspects, while the plurality of digital images are being acquired, an operator can review an image acquisition report, such as on the screen. The operator can then adjust the image acquisition process by acquiring one or more images to address any deficiencies notable in the report, such as holes, seams, etc. in the acquired depth map, for example. The image acquisition report can also provide written or spoken instructions to the operator such as, "get closer to the inner thigh and acquire more images," for example.

Wireless communications are well-suited to allow enhanced flexibility in image acquisition. For example, in the handheld method discussed hereinafter, the operator freely rotates the image capture device around the selected body part or body area of interest. With wireless communications engagement between the image capture device and a remote computing device to which the acquired digital images can be transmitted, image acquisition flexibility can be enhanced. Such wireless communication capability between the image capture device and any associated computing devices can be by one or more of Wi-Fi, Bluetooth®, RFID, cellular or the like. As would be recognized, some image capture devices will be integrated with a mobile device (e.g., smartphone, tablet, etc.), with the mobile device suitably being in wireless communication with a remote computing device. The mobile device can also be a computing device.

Referring to FIG. 4, a process 400 according to the present invention is illustrated. In a first step 405, a body part of or body area of a patient in need of treatment is selected or designated for imaging. In step 410, digital imaging of the selected body part or body area is performed, which can be rendered on a screen viewable by the operator in the form of a depth map. Such acquired images can be processed in 415 to generate a shape description—that is geometric information—of the selected body part or body area. In step 420, the shape description can be used in the diagnosis of edema, etc., such as to determine a first (or baseline) amount of edema, etc. in the patient or to generate measurement information to be used in the selection of pre-fabricated compression garments. Alternatively or, optionally, in addition to step 420, in 425 compression garments can be generated that are specifically configured for the body part or body area, to be worn on the body part or body part area at 430. A monitoring step 435 incorporates additional image acquisition 410 etc. for the previously selected and imaged body part or body area. If the generated compression garment is worn in 430, monitoring step 435 can occur to assess whether wearing such compression garment in step 430 results in an improvement or a change in a first amount of the edema, etc., that was diagnosed in 420. Still further, monitoring step 435 can be used to determine whether the wearing of such compression garment in step 430 results in an enhanced post-exercise recovery for an athlete.

In a further aspect, the inventive methods of the present invention comprise acquiring digital images of a body part or body area of interest using a four-sided imaging technique as disclosed in US Patent Application Publication No US20160235354, the disclosure of which is incorporated in its entirety by this reference. When digital images are acquired according to the methodology in the '354 Publication, shape descriptions and measurement information suitable for the diagnosis and monitoring of edema and other conditions can be obtained. Moreover, compression garments specifically configured for the patient can be fabricated from instructions derived from the shape descriptions or measurement information. To summarize the image acquisition methodology in the '354 Publication, generally:

a. The patient is positioned about 3-5 feet from a Kinect 2®, or any other suitable imaging device/computing device/software configuration, where the imaging device is positioned about 2-4 feet from the floor on a platform. The height of the imaging device is dependent, in part, of whether the upper or lower or all of the patient's body is being imaged.

b. A plurality of digital images, for example about 2 to about 20, are taken of each of the patient's front side, first side, back side, and second side of the body part or body area. If the arms are being imaged, the patient can be instructed to hold her arms at about 90 to about 60 degrees from her side. If the legs are being imaged, the patient can be instructed for image acquisition to position her legs as far apart as possible, for example to allow a gap between her thighs to be visible.

c. Once the images are acquired they can be processed to generate a shape representation of the patient body part or body area as discussed further herein.

With reference to FIG. 5, shown is a schematic block diagram of a computing device 500. In some embodiments, among others, the computing device 500 may represent a mobile device (e.g., a smartphone, tablet, computer, etc.). Each computing device 500 includes at least one processor circuit, for example, having a processor 503 and a memory 506, both of which are coupled to a local interface 509. To this end, each computing device 500 may comprise, for example, at least one server computer or like device, which can be utilized in a cloud based environment. The local interface 509 may comprise, for example, a data bus with an accompanying address/control bus or other bus structure as can be appreciated.

In some embodiments, the computing device 500 can include one or more network/communication interfaces 510. The network/communication interfaces 510 may comprise, for example, a wireless transmitter, a wireless transceiver, and/or a wireless receiver. As discussed above, the network interface 510 can communicate to a remote computing device using a Bluetooth, WiFi, or other appropriate wireless protocol. As one skilled in the art can appreciate, other wireless protocols may be used in the various embodiments of the present disclosure. In addition, the computing device 500 can be in communication with one or more image capture device(s) 521. In some implementations, an image capture device 521 can be incorporated in the computing device 500 and can interface through the locate interface 509.

Stored in the memory 506 are both data and several components that are executable by the processor 503. In particular, stored in the memory 506 and executable by the processor 503 can be a body shape description program 515 and potentially other application program(s) 518. Also stored in the memory 506 may be a data store 512 and other data. In addition, an operating system may be stored in the memory 506 and executable by the processor 503.

It is understood that there may be other applications that are stored in the memory 506 and are executable by the processor 503 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python Ruby, Flash or other programming languages.

A number of software components are stored in the memory 506 and are executable by the processor 503. In this respect, the term "executable" means a program file that is in a form that can ultimately be run by the processor 503. Examples of executable programs may be, for example, a compiled program that can be translated into machine code in a format that can be loaded into a random access portion of the memory 506 and run by the processor 503, source code that may be expressed in proper format such as object code that is capable of being loaded into a random access portion of the memory 506 and executed by the processor 503, or source code that may be interpreted by another executable program to generate instructions in a random access portion of the memory 506 to be executed by the processor 503, etc. An executable program may be stored in any portion or component of the memory 506 including, for example, random access memory (RAM), read-only memory (ROM), hard drive, solid-state drive, USB flash drive, memory card, optical disc such as compact disc (CD)

or digital versatile disc (DVD), floppy disk, magnetic tape, holographic storage, or other memory components.

The memory 506 is defined herein as including both volatile and nonvolatile memory and data storage components. Volatile components are those that do not retain data values upon loss of power. Nonvolatile components are those that retain data upon a loss of power. Thus, the memory 506 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 503 may represent multiple processors 503 and/or multiple processor cores, and the memory 506 may represent multiple memories 506 that operate in parallel processing circuits, respectively. In such a case, the local interface 509 may be an appropriate network that facilitates communication between any two of the multiple processors 503, between any processor 503 and any of the memories 506, or between any two of the memories 506, etc. The local interface 509 may comprise additional systems designed to coordinate this communication, including, for example, performing load balancing. The processor 503 may be of electrical or of some other available construction.

Although the body shape description program 515 and other application program(s) 518 described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

Also, any logic or application described herein, including the traverse and tracking program 515 and the application program 518, that comprises software or code can be embodied in any non-transitory computer-readable medium for use by or in connection with an instruction execution system such as, for example, a processor 503 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Further, any logic or application described herein, including the traverse and tracking program 515 and the other application program(s) 518, may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same computing device 500, or in multiple computing devices in the same computing environment 103. To this end, each computing device 500 may comprise, for example, at least one server computer or like device, which can be utilized in a cloud based environment. Additionally, it is understood that terms such as "application," "service," "system," "engine," "module," and so on may be interchangeable and are not intended to be limiting.

FIG. 6 illustrates a point cloud of a leg obtained by the methodology above that suitably provides a shape description of a patient who has a lymphedema grade of 1-2, where that shape description can suitably be used as set out elsewhere herein.

In a separate exemplary method of acquiring digital images from which shape descriptions of a body part or body area of interest can be obtained and from which measurement information can optionally be derived, a provider acquires patient body part or body part area digital images using a hand-held technique. Such handheld technique is useful for a wide range of edema-related conditions, such as lymphedema at stages 1-3, with stage 3 being particularly relevant to the imaging benefits resulting from this handheld methodology.

This handheld image acquisition methodology can be conducted as follows. (Note that a Structure Sensor configured with an iPad is used below, but the technique can be used with any suitable imaging device and computing device that uses a software configuration.) Image A of FIG. 7 illustrates an example of an image acquisition report, which can include information about a three-dimensional reconstruction as illustrated in the examples of images B and C, presented on a screen that is in operational engagement with the image capture device.

Arm Image Acquisition Technique (shown partially in FIG. 7):

a. The person's arm is positioned at approximately 90 degrees from her body. Generally, the angle can be less than 90 degrees if indicated by person mobility range, but for the best imaging results the angle needs to be large enough to visualize separation on the Structure Sensor/iPad combination between arm and body, which is usually a minimum of 60 degrees, depending on size of person's arm and body fat percentage.

b. The person's full arm is captured in the frame as shown on the iPad screen including hand and fingers, with the frame also being adjusted to include some of the person's body. The body serves as a relevant reference point for segmenting the arm for subsequent image processing.

c. The Structure Sensor/iPad combination is held by the operator who moves the combination laterally along the length of the person's arm while capturing views from the top, bottom, and side planes. While capturing the images, the operator can view the iPad screen to observe in real time the capture quality of the image. Such observation ability is particularly useful at the top and the bottom planes of the person's arm that have the highest risk for poor scan quality, especially in persons with complex morphologies. The operator will typically spend extra time in these areas.

d. Folds or lobes on the person can require that the operator rotate the Structure Sensor/iPad combination to capture the "underside" of the folds.

e. Each arm can be captured one at a time in order to maximize resolution of the scan.

f. Some persons can be instructed to hold onto a pole to keep their arm still or in a stable position. This can be highly useful for recent surgery or radiation persons because they often lack arm strength and range of motion.

Leg Image Acquisition Technique:

a. Person is instructed to stand with legs wide enough to achieve separation between legs in the scanning region.

b. For low-grade lymphedema, skinny legs, or scans focusing only on the lower leg, the person stance is approximately hip-width apart.

c. For higher grades of lymphedema, larger legs (especially thighs), or when the edema is concentrated in the upper leg, person stance may need to be wider.

d. Both leg images can be acquired substantially simultaneously.

e. The operator positions the segment of the legs in the scanning window as appropriate—floor to above the knee for lower leg scan and floor to above the gluteal fold for full leg scan. The operator can acquire images as she walks 360 degrees around the person while also at the same time moving the scanner up and down.

f. The inner side of the person's legs has the highest risk of poor scan quality. Because of this it is important that extra effort is taken to get a clean scan of this area. This can be done by aiming the sensor directly at the inner side of the leg and ensuring that all surfaces can be visualized.

g. Folds can require that the sensor/tablet combination rotate to capture the "underside" of the fold. This can be done by the user positioning the combination at a position that it is below the patent's skin fold and then aiming it up towards the person so the underside of the fold is acquired in a plurality of images.

Digital image acquisition by a provider's real time or substantially real-time adjustment of received images of the person's body part or body areas by movement of the imaging device in space during an image acquisition process has been found by the inventors herein to be especially useful when generating measurement information for persons with complex morphologies, such as persons with advanced edema and/or who may be obese. In this regard, it has been determined that fixed distance image acquisition setups (either with person rotating in place or camera rotating around person—even if camera or person are moving up and down) often cannot acquire accurate reconstructions of body parts or body part areas. Allowing the imaging device to freely move with six degrees of freedom, unconstrained by a mounting or support assembly, facilitates more detailed imaging of the person's body part or body areas by acquiring information at a variety of orientations and distances about the person. The freedom of movement without constraint allows the imaging to be adjusted for complexities in the surface morphology of the person.

In notable aspects, when the image capture device is rotated around the person's body part or body area, the device is not mounted to an arm or rod that rotates around a central point, such as a turntable. Still further, the person is not rotated on a platform while image capture is underway. In this way, the images are not captured along a predefined reference frame. With the image capture device able to move with six degrees of freedom, imaging of the person's body part or body area can be adapted (e.g., in real time or near real time) to ensure appropriate imaging or focusing on areas that are potentially problematic.

Using the inventive hand-held imaging methodology, the imaging device can be rotated or otherwise moved around the person's body part or body part area of interest during image capture, and the image can be reviewed by an operator who is acquiring the images in real time or the image acquisition process can be reviewed remotely substantially in real time by someone who is reviewing the image acquisition process in an offsite location. With the latter, a person can be imaged in a location remote to the medical provider, for example by herself or a family member, to allow the person's condition to be monitored at a distance, or to allow the compression therapy prescription process and/or the compression garment measurement processes to occur via telemedicine techniques.

If, when moving the imaging device around the person, the operator can determine that some portion of the person's body part or region of interest is not being well-imaged during the image acquisition step. Such lack of complete image acquisition of the body part or body area of interest may be returned on a screen to show "ridges," "holes," or "seams" in the body part or body area 3D reconstruction presented to the operator substantially in real time. By reviewing the 3D reconstruction as it is being generated during image acquisition, the operator can specifically image that area to generate an improved 3D scan for that person, where shape descriptions and, optionally, measurement information for the relevant body part or body area can be derived therefrom. This digital image acquisition and real-time review of the acquired images in relation to developing the shape description has been found to be especially useful for persons having deep tissue folds, such as for persons with advanced edema/lymphedema and/or who are morbidly obese.

In this regard, it has been found that prior art fixed plane digital image acquisition protocols (either with person rotating in place or camera rotating around person—even if camera or person are moving up and down) do not allow accurate reconstructions of tissue folds in persons. Therefore, shape descriptions and associated measurement information are not attainable therefrom. Such folds are illustrated in FIG. 2 herewith with a person presenting with an advanced stage of lymphedema, namely stage 3, in one of her legs.

With regard to the stages of lymphedema, the following information applies:
  a. Stage 0 (latent): The lymphatic vessels have sustained some damage that is not yet apparent. Transport capacity is sufficient for the amount of lymph being removed. Lymphedema is not present.
  b. Stage 1 (spontaneously reversible): Tissue is still at the pitting stage: when pressed by the fingertips, the affected area indents and reverses with elevation. Usually upon waking in the morning, the limb or affected area is normal or almost normal in size.
  c. Stage 2 (spontaneously irreversible): The tissue now has a spongy consistency and is considered non-pitting: when pressed by the fingertips, the affected area bounces back without indentation. Fibrosis found in stage 2 lymphedema marks the beginning of the hardening of the limbs and increasing size.
  d. Stage 3 (lymphostatic elephantiasis): At this stage, the swelling is irreversible and usually the limb(s) or affected area is noticeably large. The tissue is hard (fibrotic) and unresponsive; some patients consider undergoing reconstructive surgery, called "debulking". This remains controversial, however, since the risks may outweigh the benefits and the further damage done to the lymphatic system may in fact make the lymphedema worse.

Still further, lymphedema can be assessed in relation to the severity with which a clinician grades the patient's presentation:
  a. Grade 1 (mild edema): Involves the distal parts such as a forearm and hand or a lower leg and foot. The difference in circumference is less than 4 cm and other tissue changes are not yet present.
  b. Grade 2 (moderate edema): Involves an entire limb or corresponding quadrant of the trunk. Difference in circumference is 4-6 cm. Tissue changes, such as pitting, are apparent. The patient may experience erysipelas.
  c. Grade 3a (severe edema): Lymphedema is present in one limb and its associated trunk quadrant. Circumferential difference is greater than 6 centimeters. Significant skin alterations, such as cornification or keratosis, cysts and/or fistulae, are present. Additionally, the patient may experience repeated attacks of erysipelas.
  d. Grade 3b (massive edema): The same symptoms as grade 3a, except that two or more extremities are affected,
  e. Grade 4 (gigantic edema): In this stage of lymphedema, the affected extremities are huge, due to almost complete blockage of the lymph channels.

The inventors herein have determined that all stages and grades can be assessed with the handheld image acquisition technology herein, whereas the fixed platform methodology provides clinically accurate results for lymphedema stages 0-2 and grades of 1-2.

While shape description information can be used in the selection process, it has been determined herein that the methodology can also generate one or more body part circumference measurements, in addition to shape descriptions as discussed elsewhere herein. The inventors herein have determined that such improved body part circumference information can, in turn, allow improvements in the selection of pre-fabricated compression garments by a user. In this regard, when obtaining accurate 3D geometry and associated shape information for a body part, any body part circumference derivable therefrom would be conform to the actual—that is, real-life—circumference for the person including all complexity of the surface morphology.

Furthermore, the inventive methodology allows one or more body part circumferences to be oriented relative to a body region of interest to ensure accurate measurement thereof which, in turn, results in improved selection of pre-fabricated compression garments. For example, a body part circumference can be generated at a defined body location, such as the narrowest part of a wrist, with that location defined can be used as a reference point for the remainder of the body part on which the defined body part location is situated. Accordingly, one aspect of the inventive methodology herein comprises defining a location on at least one area on a body part as a reference point for fitting of a pre-fabricated compression garment.

In contrast to prior art measurement techniques, accurate generation of at least one body part circumference, with or without generation and/or use of shape description information, the present invention enhances the ability to find the best fit pre-fabricated garment(s) for the specific patient's body part. In this regard, and taking the wrist as an example, generation of an accurate body part circumference at a defined location, such as the narrowest location, can better ensure that the correctly sized compression garment is selected. If the criteria for selection of a compression garment for a person is to identify the smallest area on the body part being fitted—that is, the smallest circumference— providing of a larger circumference may result in an incorrect selection of a compression garment from the collection of compression garments. For example, if the narrowest circumference of a wrist is 8 inches, but the generated measurement is 8.5 inches, a compression garment fitting 8.5 inches would be the indicated selection. A compression garment selected for this larger wrist circumference will be larger than the patient's actual wrist circumference thus resulting in a compression garment selection that is not well-fitted to the person.

Such incorrect body part circumference measurement can result with the tape measure method when the clinician's measurement is slightly off from the intended location, which can happen with even highly trained personnel due to the highly qualitative nature of taking measurements by hand. For prior art scanning techniques, such as the Isobar Compression methodology discussed herein, down sampling of the scanner data can result in removal of the data associated with the relevant body part measurement in the analysis because such methods are not sensitive to identification of shape aspects of the body part. This could result in the incorrect measurement being provided for selection of the compression document.

Yet further, the true—or actual—geometric information for the wearer's body part being fitted for a pre-fabricated compression garment can automatically be determined for a wearer. For example, a wearer's minimum wrist circumference and/or maximum forearm circumference can be automatically derived from images of the wearer's arm. This can better ensure that a generated identification of a pre-fabricated compression garment for the wearer is, in fact, an accurate selection for that wearer. To this end, if a wearer has a complex body morphology, such as a lobe, fold, or well-developed muscle architecture in a location away from the location where a standard measurement for a pre-fabricated compression garment as shown, for example, in FIGS. 8 and 9, the standard measurement technique may not identify a garment that will be effective for that wearer. Such a garment may be ill-fitting, such as being too tight, thus reducing the likelihood that the wearer will consistently wear the garment, as well as likely reducing the effectiveness of the garment due to incorrect pressure application.

Moreover, using standard compression garment fitting methodology, observation of a complex surface morphology may result in a recommendation that the wearer be fitted for an expensive and time-delayed custom compression garment. The inventive methodology can be used to automatically identify a plurality of circumferences along a length of a wearer's body part being fitted with a pre-fabricated compression garment so as to allow identification of a mis-match between an expected wearer body part circumference along a length of the body part and a corresponding circumference on a pre-fabricated compression garment. For example, if a person being fitted for a compression garment in the form of an arm sleeve has wrist, forearm, elbow and arm pit measurements that indicate that a particular pre-fabricated compression garment is the correct size, but the wearer has an abnormally prominent bicep area, the inventive methodology can incorporate such information in an identification (or not) of a pre-fabricated compression garment appropriately fitted for that wearer. Information can be provided to that wearer directing the selection of an appropriately fitted pre-fabricated garment from a plurality (or collection) of garments.

As discussed previously, body part information obtained according to the present invention can also be used to fit pre-fabricated compression garments for a wearer to provide an improved fitting methodology. The inventive methodology allows accurate measurement information to be obtained for one or more body parts or body areas of interest (e.g., arm, leg, trunk, neck, etc.). The measurement methodology of the present invention provides substantially accurate anthropometric measurements, as well as high resolution information for the relevant body part or body part areas so as to enable excellent reproductions of the person's physique, especially in relation to a person's specific muscle architecture. Furthermore, the invention enables body part measurements to be obtained without the typical inter-operator error, thereby better standardizing the resultant fit and subsequent performance of the compression garments.

In a significant aspect, the inventive methodology herein provides improvements in the selection of pre-fabricated compression garments for a person in need of compression treatment on at least one body part. In the specific context of pre-fabricated garments, the inventive methodology enables more accurate and more consistent set of derived measurements to inform sizing of pre-fabricated compression garments and selection thereof, which would subsequently ensure a better fit and a better performing garment. Off the shelf compression garments—that is, those not based on custom patient body specifications—must necessarily each be sized to fit a reasonable number of people for each SKU, at least because retailers require that the number of SKUs be rationalized for each supplier. People's body parts are far from standardized, however. A 6 foot, 200 pound man who is a body builder will likely have a very different arm muscle architecture than a male swimmer of the same height and weight. In this example, it can be seen that the current use of generalized compression garment sizing that is directed toward reduction of SKU number in a retail environment can allow each of these athletes to obtain compression garments that are suitably sized to provide effective post-exercise compression treatment.

To this end, pre-fabricated medical compression garments are manufactured and available in a range of standard sizes, which are selected for a patient based on their limb circumference and limb length measurements. Each measurement has a range that corresponds to a certain size. Each major brand has a specific fitting guide for each type of compression garment they provide, and the selection of garments both within and among manufacturers can be a complex and confusing endeavor. The specific manufacturer guides explain which circumference measurements are required for selecting the best fit ready to wear garment that they supply. Measurements usually contain anatomical landmarks such as the smallest circumference at the ankle and the largest circumference at the calf. The clinician or trained fitter will physically inspect the patient during a visit and obtain the appropriate measurements according to the size guide. Garments can be selected for arms, hands, legs and feet, for example.

Pre-fabricated garments are each usually available in different compression ranges. To ensure proper fitting, these garments typically require a clinician or a "certified fitter" trained in measuring limbs for fitting garments to measure a person's limb circumference at different locations along the length thereof according to a fitting guide for each specific garment brand and style. The pre-fabricated garment is then selected based on a "best fit" match between the generated measurements and the available pre-fabricated garments.

The inventive methodology can be used to obtain the required measurements needed to select the best size of pre-fabricated garment from a collection of compression garments. Such is a significant improvement over the prior art. The generated measurement information, which includes at least limb measurement information, is compared to provided measurements associated with the collection of pre-fabricated compression garments. A best-fit match between the generated user body part measurements and the measurements of each of the collection of pre-fabricated compression garments is provided, whereby at least one pre-fabricated compression garment is identified for selection by the user from the collection.

Yet further, the inventive methodology also allows automation and standardization of a wearers anatomic landmarks and associated circumferences and, in some aspects, length measurements—that is, information pertinent to compression garment sizing—in the region of such identified landmarks and areas proximate thereto. Once a wearer's measurements are obtained in a first wearer data collection step, the information can be stored for later use. These stored user measurements can be recalled at a later time for use in a subsequent compression garment fitting operation. Such stored information can also be recalled at a later time to assess whether the wearer's body part circumferences have changed between measurement events. This can facilitate determination of whether the wearer has experienced improvement or lack thereof in actual or potential edema-related conditions, for example.

In some aspects, the invention comprises selecting a pre-fabricated compression garment from a plurality (or collection) of pre-fabricated compression garments. The plurality (or collection) can be from a single manufacturer or a plurality of manufacturers. When from a single manufacturer, the best fit from a single source can be identified for a user. When from a plurality of manufacturers, the user can be provided with the best fit from a variety of manufacturers.

The information derived from a collection of wearer measurements obtained from the inventive methodology can be incorporated into a database of information. Analysis of such database can be used to generate a library of measurements that can be deployed to generate patterns for pre-fabricated compression garments, as well as compression garments generated therefrom.

In providing the identification to a user for selection, digital images of a selected body part are acquired as set out elsewhere herein. While a variety of pre-fabricated compression garments can be fitted for a wearer in accordance with the present invention, compression garments configured for use on an arm or a leg are particularly well suited for the present invention. For example, pre-fabricated compression garments similar to those pictured for the arm and leg in FIG. 3 herewith can be suitably fitted.

In order to fit the pre-fabricated compression garments to a wearer, a first wearer outer circumference measurement is generated from the digital images. The methodology can automatically determine the relevant body part area for use in determining the wearer circumferences to be used in identification of an appropriate pre-fabricated compression garment for that wearer. As shown in FIG. 8, for arm compression garments, the circumference of wearer arm 800 can be generated at fit locations that are the wearer's wrist area 805, forearm area 810, elbow area 815, upper arm area 820 and axilla area 825. The number and location of the circumference measurements can be dependent on whether the arm sleeve is for the lower arm only (i.e., length 830) or it is for the whole arm (i.e., lengths 830 and 835). To generate the circumference of the wearer's wrist 805 for an arm sleeve, for example, the circumference of the narrowest part of the wrist can be generated via image processing as discussed herein. As shown in FIG. 9, for a compression stocking for leg 900, the circumference of ankle area 905 can be generated via image processing, as well as the widest calf circumference 910 and knee circumference 915. Further as shown in FIG. 9, if a compression pantyhose is the garment to be fitted, circumference measurements at the widest portion of thigh 920 and at hip 925 can be taken in addition the lower leg measurements. As noted previously, the locations where such circumference measurements are obtained can be generated automatically via processing of the images according to the inventive methodology.

In order to identify the best fit for a wearer, dimensions for the plurality of pre-fabricated compression garments are obtained, where a plurality of circumference measurements for each of the garments is derivable therefrom. The plurality of circumference measurements are taken along a length of the compression garment. For example, for a full arm compression garment, measurements can be taken at least the wrist area, the forearm area, the elbow area and the armpit area, where such areas are in relation to where the compression garment will fit on the wearer. More circumferences can be generated along the length of the compression garment.

Generally, a compression garment for treatment of edema-like conditions will be very thin, for example, about 1 or 2 mm, such that the inner circumference and the outer circumference of a pre-fabricated compression garment will be essentially the same. Such circumference measurements can be generated from, for example, specifications used to fabricate the compression garments via computerized knitting operations, as discussed hereinafter. If the pre-fabricated compression garment comprises a fabric or other type of outer cover, such as might be the case with a compression garment that is intended for exercise or the like, the thickness may be such that the inner circumference and outer circumference of the compression garment will not be essentially the same. In this case, the inner circumference of the garment will serve as the measurement circumference reference point. Yet, further, the inner circumference is the baseline of measurement for the compression garment to eliminate any differential between the inner and outer circumference measurements for the pre-fabricated compression garments. Still further, such garment circumference measurements can be obtained from physical measurement of the inner and/or outer circumferences of a plurality of pre-fabricated compression garments and incorporation of the results into software instructions associated with the inventive methodology. This latter measurement method is particularly useful when the identification of a pre-fabricated compression garment from is from a plurality of compression garments for which computerized information is not directly obtainable, such as for compression garments that are made by different manufacturers.

At least a first circumference measurement at a first wearer fit location is derivable from the provided compression garment dimensions. In some aspects, a second circumference measurement at a second wearer fit location is derivable from the compression garment dimensions. Still further, three, or four, or more circumference measurements at three, or four, or more second fit locations are derivable from the compression garment dimensions. At least two or more wearer fit locations and garment fit locations can be generated for each selected body part. Indeed, a large number of circumferences can be generated along the length of the body part, and these circumferences can be associated with the same number or fewer of circumferences on a pre-fabricated compression garment.

To identify the best fitting pre-fabricated compression garment for a wearer from a plurality (or collection) of pre-fabricated compression garments, each of the derived circumference measurements at the first garment fit location for each of the plurality of pre-fabricated compression garments is compared to the first wearer fit location circumference. The wearer fit location circumference that is closest to the compression garment circumference is identified as the best fit and information is provided to the user. Such identification can be provided to allow selection thereof for use.

To obtain a good match between the wearer body part and the pre-fabricated compression garment so as to ensure effective compression therapy, the wearer fit location and the garment fit location are the same, in substantial aspects. For example, the wearer fit location can be at or near the narrowest part of a wearer's wrist, and the garment fit location is at or near the same wrist location as configured in the compression garment. Or the wearer fit location can be at or near the wearer's elbow, and the garment fit location is at or near the elbow location configured into the compression garment. Still further, the wearer fit location can be at or near the wearer's ankle, and the garment fit location is at or near the ankle location configured into the compression garment. Or the wearer fit location can be at or near the wearer's knee, and the garment fit location is at or near the knee location configured into the compression garment. Any other location on the wearer's arm or leg can be the provided circumference as the wearer fit location, with the garment fit location associated therewith also being the same.

Referring to FIG. 10, a process 1000 for fitting a pre-fabricated compression garment for a wearer according to the present disclosure is illustrated. In a first step 1005, a body part of or body area of a patient or wearer is selected or designated for imaging to fit a compression garment. In step 1010, digital imaging of the selected body part or body area is performed, thereby acquiring digital images of the body part. Such acquired images can be processed in 1015 to generate a shape description information for the selected body part or body area, from which wearer body part circumferences are derivable. One or more wearer fit location outer circumference measurements can be generated for the body part. A length for the wearer body part can also be determined. In step 1020, dimension information for one or more compression garments (e.g., pre-fabricated compression garments) can be provided. The dimension information can include, but is not limited to, circumference measurements for the garment fit locations and/or the garment length measurement. In 1025, the garment measurements of the compression garments can be compared with the wearer fit location circumference measurement and/or the length of the wearer body part and used to identify at least one compression garment at 1030. The identified compression garment or garments can be those having a garment fit circumference measurement that is closes to the corresponding wearer fit location circumference measurement. In addition, the garment can have a length measurement that is closest to the wearer body part length. The identified compression garment can be supplied to the wearer at 1040.

In some aspects, the wearer imaging can be conducted in a first location, and orientation of the imaging device relative to the wearer can be operated wholly or in part from a second location, that is, remotely. Such a configuration can allow identification of an appropriately sized pre-fabricated compression garment without the wearer having to travel to another location or for a person to travel to the location of the wearer to acquire the images. When the wearer is at a remote location from the operation of the image acquisition process, instructions can be provided to the wearer of how to place her body part to allow images suitable to generate the at least one wearer outer body part circumference to be generated. Such instructions can be verbal or provided on a screen visible to the wearer during the image acquisition process.

Processing of the image acquisition steps is generally conducted automatically by the computer such as, e.g., the computing device 500 of FIG. 5. Instructions provided to the wearer on how she should position her body part can also be generated automatically by the computer as a result of image processing that indicates that the images acquired do not yet allow a suitable wearer location fit circumference to be generated. Alternatively, remote instructions during the image acquisition process can be from a human operator who is observing the image acquisition process remotely in real time. Still further, instructions provided to the wearer during the image acquisition process are provided in by both automatically by a computer and by a human operator observing the image acquisition process remotely.

As noted, wearer body fit location circumferences can be associated with one of a plurality (or collection) of pre-fabricated compression garments. Typically, pre-fabricated compression garments are sized according to relevant fit circumferences, such as ankle and calf for calf height compression stockings. One such calf height sock is a Traverse™ knee high sock. (Sigvaris, St. Gallen, CH). Body location fit circumferences in the pre-fabricated compression garments according to a manufacturer-specific sizing implementation. As an illustrative example, for the ankle circumference the Traverse knee high socks use "small" (7 to 8.5 inches), "medium" (8.5 to 10 inches), "large" (10 to 11.5 inches), and "extra large" (11.5 to 14 inches). For the calf circumference the Traverse knee high socks use "small" (11 to 15.5 inches), "medium" (12.5 to 17.5 inches), "large" (14 to 20 inches), and "extra large" (16 to 24 inches). Plus sizes are also available. For compression pantyhose, additional circumferences for the widest portion of the wearer's thigh and hip will be obtained. For pre-fabricated arm compression garments, measurements will be taken at the wrist and below the elbow for gauntlet-type garments, and above the elbow for full sleeved garments. Again, each manufacturer will have its own set of sizing parameters, and such sizing parameters will be included in the dimension information used in the inventive methodology.

As for a leg compression garment, the circumferences of various leg locations are typically generated and the manufacturer's fit chart is reviewed to match the fit to the wearer arm measurements. For fitting of Juzo® arm sleeve (Cuyahoga Falls, Ohio), six different size options are provided, plus additional options for larger cupper arm and elbow circumferences. Two different length options, "regular" with a wrist to armpit length of <43 centimeters and a long for a wrist to armpit length of >43 centimeters are provided.

In order to select an appropriately fitted pre-fabricated knee high compression stocking using prior art methods, the user will also have to measure each of her ankle at the correct location, and her calf at the widest location, and then use a selection chart, that will also include length measurements. The body part circumferences generated from the inventive image acquisition and processing methodology herein allows a user to obtain information about what size pre-fabricated compression garment should be selected without having to go through complicated physical measurement steps and product identification steps.

As provided by the fit instructions for the compression knee highs shown above, two or more locations for the wearer body part circumference can be generated, as well as a length. For the compression pantyhose, four locations for the wearer body part circumference are generated, as well a length to the wear's gluteal fold. For an arm sleeve compression garment, five wearer body part outer circumferences can be generated, namely under the axilla or armpit region, the middle of the upper arm, the elbow, the middle of the forearm, and the wrist. For a partial sleeve arm compression garment, two wearer body part outer circumferences can be generated, namely the wrist and the elbow. For a glove, two body part outer circumferences, namely the base of the four fingers under the thumb and the wrist can be generated. Lengths for the fingers, forearm, and upper arm to the armpit can also optionally be generated to ensure a better fit lengthwise. As noted, the inventive methodology allows such circumferences to be automatically generated, as well as their location on a specific wearer's body part. The length of the specific wearer's body part can be automatically generated, also.

In addition to body part circumferences, the image acquisition and processing steps can provide relevant lengths of the body parts being fitted with the pre-fabricated compression garments. Such length measurements are shown, for example, as 830 and 835 in FIG. 8, and 930 and 935 in FIG. 9. Again, the enhanced information generatable from the inventive processes herein provide more accurate fitting than available with prior art imaging methods, at least because down sampling of these images during the processing steps. Such length measurements will ensure an adequate fit along the entire body part. For example, for leg height compression socks, the calf length can be associated with a "petite" garment (≤14 inches), a "short" garment (≤16 inches), a "medium" garment (≥16 inches).

While the length of the relevant body part can be automatically generated from the image generation and processing methodology of the present invention, to the extent that body part length is relevant to the identification of pre-fabricated compression garments, such length can be obtained by other techniques. For example, a wear's height can be incorporated as a selection or input parameter in the software instructions where the wearer or an operator can be asked to provide such height. Or a wearer can select or input a pants leg size. Or a ruler or measurement can be used, such as a laser measuring device, and body part length information so generated can be used in the pre-fabricated garment selection process.

Manufacturers of pre-fabricated compression garments generally include a variety of selectable parameters in a collection of garments within a product line. Accordingly, in some aspects, the present invention will also incorporate selection of one or more of the compression level (e.g., 10 to 20 mm Hg, 20 to 30 mm Hg, 30 to 40 mm Hg, 40 to 50 mm Hg, or 50 to 60 mm Hg, or any range of endpoints), fabric/material (nylon, wool, rubber), color (by skin tone level, white, or black), open or closed toe for leg, gloved or ungloved for arm, shoe size, and wearer gender. Such information can be incorporated as selection or input criteria presented to the wearer or operator to further simplify the fitting process for a wearer. Further, information about wearer identity and preferences can be maintained in the system for subsequent selection processes.

In notable aspects, the methodology herein allows the generation of highly accurate geometric information for a patient's body part or body area of interest by generating one or more shape descriptions for that body part or body area. Generation of shape descriptions for the body part or body area of interest in a specific patient provide significantly enhanced measurement information as compared to the traditional circumference and length measurements used to generate compression garments. Accordingly, the inventive methodology can be used to generate accurate, geometrically-based, 3D representations for a specific patient body part or body area of interest.

Notably, the methodology of the present invention allows substantially accurate shape description information, which also includes body part circumference information derivable therefrom, to be generated in virtually any location at which the patient might be located using the image generation and processing methodologies disclosed elsewhere herein. The relative simplicity of generating the digital images from a specific patient means that it is possible for patients to take their own images in convenient locations. The increased simplicity provides a previously unrealized ability to enable regular monitoring of patient body part or body area measurements, for example, a home setting or in other extra-clinical settings, thereby greatly enhancing the ability to generate and maintain properly fitted compression garments, be they for therapeutic treatment or otherwise. Because the person can be measured, and therefore fitted, in their home or other private location, access to well-fitting compression garments for various uses can be greatly enhanced.

Yet further, one or more or of a plurality of body contour measurements derived from one or more shape descriptions of a body part or body area of interest can be combined to form a compression garment configured for wearing by a user. For example, the compression garment of the invention may comprise shorts, long tights or tops, either as a single garment or in a combination of garments intended to be worn as a suit. As an example, an athlete may have arms or legs of different exterior contours due to dominance, injury or other factors. The improved measurement capabilities disclosed herein can enable custom bicycle pants to be generated for a cyclist with the legs precisely fit to the volume of that person when the measurement information is provided to generate a pattern or other information suitable to manufacture such a garment. The present invention can also be utilized to generate custom-fitted swimsuits or other athletic apparel where compression comprises at least a part of the functional aspect incorporated into such garment. Using the body part circumference information obtainable from the present invention, the selection of pre-fabricated athletic clothing can be enhanced. For example, a pre-fabricated swim garment having circumference information associated therewith can be identified as being the best fit for a specific wearer.

The material of which the compression garment of the invention is made may be chosen from a wide variety of fabric or different fabrics. In some aspects, the garment of the invention can be made of panels of fabrics of elastane or similar stretch material, often combined with nylon or polyester or similar stretch materials of 40, 60 or up to 120 denier material. The fabric can comprise selected stretch and recovery characteristics. The stretch along the warp of the fabric can be from about 120% to about 225% and its number for recovery is from about 10% to about 25%. The material can incorporate a "wicking" effect, so that in use it draws moisture from the body. Such materials are known.

As would be recognized, modern knitting machines are highly integrated with processing controls and software. In this regard, the highly accurate measurement information generated from the disclosed herein can be incorporated in the compression garment fabrication instructions associated with use of the knitting machine. Such fabrication instructions can be transmitted by the imaging devices and associated equipment via the cloud. Alternatively, the measurements can be provided to the knitting machine by uploading the measurements on a USB device or the like, as would be known.

Compression garments generated from fabrication information generated by the inventive methods herein can be made from thicker (but breathable) materials and knitted row by row as a flat piece, which are shaped and produced by adding or removing needles during the production process, according to the exact measurements of the person. The finished flat piece can then be joined by a seam to form the garment. Such heavier knit materials can provide greater stiffness resulting in greater resistance and better containment of the swelling than ready-made garments (so-called stiffness factor). As such, such thicker materials are more suitable for applications where a higher compression value is required, such as for lymphedema treatment.

Still further, compression garments generated from the inventive fabrication information can be prepared in one piece, such as from a continuous knitting machine.

Yet further, the inventive measurement methods can be utilized to provide compression garments with lower compression values, which might be more suitable for sport-type applications. In this regard, relatively thin and sheer fabrics that are continually knitted in a circular fashion on a cylinder and thus have no seam. As would be recognized, varying stitch height and yarn tension create the appropriate shape and size based on the measurements provided in the manufacture thereof.

The present invention can also comprise patterns for use in preparing compression garments. Such patterns and any associated compression garments will be specifically associated with the body features of the person being fitted for, and therefore treated with, the compression garment. Still further, the methodology herein can be used to select a pre-fabricated compression garment of a predetermined size, that is, an "off the shelf" or "ready to wear" garment.

Various designs or constructions can be included in the compression garment to provide improved functionality relating to compression activity. For example, US Patent Application Publication No. 20140200494, the disclosure of which is incorporated herein in its entirety by this reference provides a purported improved functionality based upon the knitted pattern in the resulting garment. Yet further, U.S. Pat. No. 9,345,271, the disclosure of which is incorporated herein in its entirety by this reference, illustrates how variable pressure can be generated along the length of a compression garment via stitching techniques. Yet further, compression garments of the present invention can comprise a plurality of panels having variable compression fabric within or added over panels of other compression fabric to generate improved muscle support. Still further, the methodology of the present invention allows measurements to be generated to provide compression garments where compression can be placed in particular on some joints or muscles. This, in turn, allows incremental compression to be achieved in the garment. Such incremental compression has been found to increase strength and stability on the joints, whilst supporting the muscles. This is a variation on the existing art where the support can be invoked by the wearer, choosing between an active state and a passive state. Such varied compression features can be identified for incorporation as a result of the improved limb or body part shape possible by the measurement techniques of the present invention.

In addition to the measurement information generated from the person, features relevant to the garment construction can also be incorporated into the information used to create the compression garment specifically configured to fit the person. In this regard, the information used to fabricate each compression garment can further include a desired compression, a desired compression class, whether the compression need is for prophylaxis, a degree of edema or vascular insufficiency of the person, or an indication of compression sensitivity of the person, such as if the person has a skin condition where compression might cause damage to the person. Where the additional information is a positive indication of compression sensitivity of the person, the expected compression of the given garment can be a lowest expected compression of a set of garments with acceptable expected compression, and the given garment can be determined to meet the compression need of the person in response to the positive indication of compression sensitivity.

In further aspects, the compression garments generated according to the methodology herein can be configured with a plurality of sensors. The sensors can be utilized to measure and/or diagnose muscle behavior in a person, such as by assisting in the evaluation of an athlete's performance, as disclosed in US Patent Application Publication No. 20140259267, the disclosure of which is incorporated herein in its entirety by this reference. Yet further the one or plurality of sensors can incorporate functionality that provides therapeutic benefits to a user. In such latter example, the selective constriction and dilation disclosed in US Patent Application Publication No. 20160120734 is illustrative, of which the disclosure therein is incorporated herein in its entirety.

In one or more aspects, the sensors can be positioned in one or a plurality of locations on a compression garment generated for use on a person's leg. For example, the one or a plurality of sensors can be positioned proximal to the person's vastus lateralis, vastus medialis; vastus intermedius, rectus femoris, biceps femoris, semimembranosus, semitendinosus, gastrocnemius, soleus, or plantaris. Yet further, the one or plurality of sensors incorporated in or associated with the compression garment can be positioned in one or a plurality of positions on a generated for use on a person's arm. In this regard, the one or plurality of sensors incorporated in or associated with the compression garment can be positioned proximal to the persons' biceps, triceps, brachioradialis, extensor carpi, radialis longus, or deltoid. As described elsewhere herein, the improved measurements possible with the inventive methodology herein provide improved fit for the compression garments. Similarly, placement of the sensors in the compression garments will be improved because the anthropometric measurement techniques of the present invention can generate better identification of the relevant locations of a person's arms or legs.

While the present invention is primarily directed toward improved fitting of compression garments, and garments made therefrom, the present invention can also be used to generate anthropometric measurements for use to create custom clothing. The variety of garments that can be generated from the inventive anthropometric measurement techniques are expansive, and are limited only by the desire of persons to have access to custom-fit garments. In non-limiting examples, the inventive measurement techniques herein can be used to generate dresses, suits, trousers, jackets, shapewear, jeans, and the like. The anthropometric measurements can be provided to a pattern engineer to generate custom clothing, that is clothing that is created from a pattern generated from the measurements of a person for whom the garment is intended to be worn. With the proliferation of computerized sewing methods, such as those available in the near future from SoftWear Automation (Atlanta, Ga.), the anthropometric measurement methods of the present invention will increase the accessibility of custom clothing to the public. Methodologies for generating custom-fit clothing from a person's measurements are disclosed, for example, in US Patent Application Publication No. 20140277663, the disclosure of which is incorporated herein in its entirety by this reference.

Yet further, the measurement methodology of the present invention can be used to improve selection of ready to wear clothing for a person. In this regard, the anthropometric measurements obtained can be input into a look up table, for example, to provide improved fit selection for a person. As an example, a person can obtain measurements that can be matched with the dimensions (or fit characteristics) of various clothing types to reduce uncertainty in determining whether a particular type of clothing will fit the person. Such improved fit probabilities can facilitate purchases of clothing online, for example. One example of improved fit methodologies that can be utilized with the anthropometric measurement methodology of the present invention is illustrated in U.S. Pat. No. 7,398,133, the disclosure of which is incorporated herein in its entirety by this reference.

A number of embodiments have been described but a person of skill understands that still other embodiments are encompassed by this disclosure. It will be appreciated by those skilled in the art that changes could be made to the embodiments described above without departing from the broad inventive concepts thereof. It is understood, therefore, that this disclosure and the inventive concepts are not limited to the particular embodiments disclosed, but are intended to cover modifications within the spirit and scope of the inventive concepts including as defined in the appended claims. Accordingly, the foregoing description of various embodiments does not necessarily imply exclusion. For example, "some" embodiments or "other" embodiments may include all or part of "some", "other," "further," and "certain" embodiments within the scope of this invention.

What is claimed is:

1. A method for monitoring a body part of interest of a person, comprising:
   a) selecting a body part of a person;
   b) acquiring, in a baseline imaging event, a plurality of baseline digital images of the selected body part, wherein the plurality of baseline digital images are acquired along at least part of a length of the selected body part, wherein the plurality of baseline digital images are acquired by an operator or a device by moving an imaging device around and along the selected body part, and wherein an image acquisition report is presented on a screen that is in operational engagement with the imaging device; and
   c) processing, by a computer, the plurality of baseline digital images to derive baseline shape description information for the selected body part,
   thereby generating selected body part information configured for:
      i) selection of a first pre-fabricated compression garment; or
      ii) generation of a first custom-fitted compression garment.

2. The method of claim 1, further comprising:
   a) acquiring, in a subsequent imaging event, a plurality of subsequent digital images of the selected body part, wherein the plurality of subsequent digital images are acquired along at least part of the length of the selected body part;
   b) processing, by the computer, the plurality of subsequent digital images to derive subsequent shape description information for the selected body part;
   c) comparing the baseline shape description information with the subsequent shape description information; and
   d) determining whether there is a change between the baseline shape description information and the subsequent shape description information, thereby generating information configured for:
      i) selection of a second pre-fabricated compression garment; or
      ii) generation of a second custom-fitted compression garment.

3. The method of claim 2, further comprising incorporating the generated information about the change between the baseline shape description information and the subsequent shape description information into an edema or a lymphedema diagnosis.

4. The method of claim 2, wherein morphology information for the selected body part is derivable from either or both of the baseline shape description information or the subsequent shape description information.

5. The method of claim 2, wherein information is provided to a user from each of the baseline shape description information and the subsequent shape description information, and wherein the generated information indicates whether the change exists between the baseline shape description information and the subsequent shape description information for the selected body part, thereby allowing determination of whether wearing of the first pre-fabricated compression garment or the first custom-fitted compression garment by the person resulted in a change in a previous diagnosis of edema or lymphedema in the person.

6. The method of claim 2, wherein information is provided to a user from each of the baseline shape description information and the subsequent shape description information, and wherein the provided information indicates whether a change exists between the baseline shape description information and the subsequent shape description information for the selected body type, thereby allowing a determination of whether wearing of a first pre-fabricated compression garment or the first custom-fitted compression garment by the person resulted in a change in a geometric shape of the selected body part between the baseline imaging event and the subsequent imaging event.

7. The method of claim 1, wherein:
   a) the generated selected body part information is used in a selection of the first pre-fabricated compression garment or in a generation of the first custom-fitted compression garment as a compression garment for an arm of the person;
   b) the compression garment is in the form of an arm sleeve; and
   c) the compression garment is configured to apply a compression value to at least part of the arm of the person in a range from 10 to 50 mm Hg.

8. The method of claim 1, wherein:
   a) the generated selected body part information is used in a selection of the first pre-fabricated compression garment or in a generation of the first custom-fitted compression garment as a compression for a leg of the person;
   b) the compression garment is in the form of a leg sleeve; and
   c) the compression garment is configured to apply a compression value to at least part of the leg of the person in a range from 10 to 50 mm Hg.

9. A method for monitoring a body part of interest of a person, comprising:
   a) selecting a body part of a person;
   b) acquiring, in a baseline imaging event, a plurality of baseline digital images of the selected body part, wherein the plurality of baseline digital images are acquired along at least part of a length of the selected body part;
   c) processing, by a computer, the plurality of baseline digital images to derive baseline shape description information for the selected body part,
   d) acquiring, in a subsequent imaging event, a plurality of subsequent digital images of the selected body part, wherein the plurality of subsequent digital images are acquired along the at least part of the length of the selected body part;
   e) processing, by the computer, the plurality of subsequent digital images to derive subsequent shape description information for the selected body part;
   f) comparing the baseline shape description information with the subsequent shape description information; and
   g) determining whether there is a change between the baseline shape description information and the subsequent shape description information.

10. The method of claim 9, wherein either or both of the baseline shape description information or the subsequent shape description information is configured as compression garment fit information for the selected body part for:
   i) selection of one or more pre-fabricated compression garments; or
   ii) generation of one or more custom-fitted compression garments.

11. The method of claim 9, further comprising incorporating generated information about the change between the baseline shape description information and the subsequent shape description information between the baseline imaging event and subsequent imaging events into an edema or a lymphedema diagnosis.

12. The method of claim 9, wherein a plurality of subsequent shape descriptions is derived, thereby allowing a progression of changes in the plurality of subsequent shape descriptions of the selected body part to be monitored over time.

13. The method of claim 9, wherein shape description information is provided to a user from each of the baseline shape description information and the subsequent shape description information, and wherein the provided shape description information allows a determination of whether wearing of a selected pre-fabricated compression garment or of a custom-fitted compression garment resulted in a change from a previous diagnosis of edema or lymphedema in the person.

14. The method of claim 9, wherein a plurality of subsequent shape descriptions is generated, thereby allowing a progression of changes in a shape of the selected body part to be monitored over time.

15. The method of claim 9, wherein shape description information is provided to a user from each of the baseline shape description information and the subsequent shape description information, and wherein the provided shape description information allows a determination of whether wearing of a selected pre-fabricated compression garment or of a custom-fitted compression garment resulted in a change in a geometric shape of the selected body part.

16. A method for monitoring a body part of interest of a person, comprising:
  a) selecting a body part of a person;
  b) acquiring, in a baseline imaging event, a plurality of baseline digital images of the selected body part, wherein the plurality of baseline digital images are acquired along at least part of a length of the selected body part;
  c) processing, by a computer, the plurality of baseline digital images to derive baseline shape description information for the selected body part;
  d) generating, by the computer, compression garment fit information for the person;
  e) acquiring, in a subsequent imaging event, a plurality of subsequent digital images of the selected body part, wherein the plurality of subsequent digital images are acquired along the at least part of the length of the selected body part;
  f) processing, by the computer, the plurality of subsequent digital images to derive subsequent shape description information for the selected body part;
  g) comparing the baseline shape description information with the subsequent shape description information; and
  h) determining whether there is a change between the baseline shape description information and the subsequent shape description information.

17. The method of claim 16, further comprising generating, by the computer, second compression garment fit information for the person if the change is determined between the baseline shape description information and the subsequent shape description information.

* * * * *